(12) United States Patent
Ohgi et al.

(10) Patent No.: US 7,655,768 B2
(45) Date of Patent: Feb. 2, 2010

(54) GALACTOSE DERIVATIVE, DRUG CARRIER AND MEDICINAL COMPOSITION

(75) Inventors: Tadaaki Ohgi, Tsuchiura (JP); Toshihiro Ueda, Tsukuba (JP)

(73) Assignee: Nippon Shinyaku Co., Ltd. (JP)

( * ) Notice: Subject to any disclaimer, the term of this patent is extended or adjusted under 35 U.S.C. 154(b) by 193 days.

(21) Appl. No.: 11/574,302

(22) PCT Filed: Aug. 25, 2005

(86) PCT No.: PCT/JP2005/015424

§ 371 (c)(1),
(2), (4) Date: Feb. 26, 2007

(87) PCT Pub. No.: WO2006/022325

PCT Pub. Date: Mar. 2, 2006

(65) Prior Publication Data

US 2007/0244058 A1 Oct. 18, 2007

(30) Foreign Application Priority Data

Aug. 26, 2004 (JP) .............................. 2004-246190

(51) Int. Cl.
*C07G 3/00* (2006.01)
*C07G 11/00* (2006.01)
*C07H 15/00* (2006.01)
*C07H 17/00* (2006.01)
*A61K 31/70* (2006.01)
*A61K 9/127* (2006.01)
*A01N 43/04* (2006.01)

(52) U.S. Cl. .......................... 536/4.1; 514/25; 424/450
(58) Field of Classification Search .................. None
See application file for complete search history.

(56) References Cited

FOREIGN PATENT DOCUMENTS

| EP | 0 685 234 | 12/1995 |
|----|-----------|---------|
| EP | 0 685 457 | 12/1995 |
| JP | 06-080560 | * 3/1994 |
| JP | 6-271597 | 9/1994 |
| JP | 7-188274 | 7/1995 |
| JP | 9-235292 | 9/1997 |
| WO | 02/055692 | 7/2002 |
| WO | 02/055693 | 7/2002 |

OTHER PUBLICATIONS

G. Pohlentz, et al., 1-Deoxy-1-phosphatidylethanolamino-lactitol-type neoglycolipids serve as acceptors for sialyltransferases from rat liver golgi vesicles, European Journal of Biochemistry, 1992, 203 (3), pp. 387-392.

(Continued)

*Primary Examiner*—Shaojia Anna Jiang
*Assistant Examiner*—Scarlett Goon
(74) *Attorney, Agent, or Firm*—Darby & Darby, P.C.

(57) ABSTRACT

The present invention relates to a novel and useful galactose derivative constituting a drug carrier by which a medicine can be efficiently transferred into the liver, a drug carrier comprising the derivative, and a pharmaceutical composition comprising the carrier and a medicine. The present invention also relates to a galactose derivative made up of galactose, a suitable spacer and a certain lipid, a drug carrier comprising the derivative and a cationic lipid, and a pharmaceutical composition comprising the carrier and a medicine (preferably a double-stranded RNA, a double-stranded DNA, or an oligo nucleic acid).

8 Claims, 4 Drawing Sheets

OTHER PUBLICATIONS

G. Pohlentz, et al., Neoglycolipids Derived from Phosphatidylethanolamine Serve as Probes in Cell Culture Studies on Glycolipid Metabolism, Biological Chemistry, 2000, 381 (1), pp. 29-34.

G. Pohlentz, et al., [13] Neoglycolipids of 1-Deoxy-1-phosphatidylethanolaminolactitol Type: Synthesis, Structure Analysis, and Use as Probes for Characterization of Glycosyltransferases, Methods in Enzymology, 1994, 242, pp. 127-145.

Zhong Xu, et al., Synthesis and Characterization of Oligomaltose-Grafted Lipids with Application to Liposomes, Journal of Colloid and Interface Science, 2002, 252 (1), pp. 57-65.

M. Spiess, The Asialoglycoprotein Receptor: A Model for Endocytic Transport Receptors, Biochemistry, 1990, 29, pp. 10009-10018.

S. Kawakami, et al., Asialoglycoprotein Receptor-Mediated Gene Transfer Using Novel Galactosylated Cationic Liposomes, Biochemical and Biophysical Research Communications, 1998, 252, pp. 78-83.

International Preliminary Report on Patentability date unknown issued during the prosecution of International Patent Application No. PCT/JP2005/015424.

Peng Wang, et al., Synthesis of Phospholipid-Inhibitor Conjugates by Enzymatic Transphosphatidylation with Phospholipase D, J. Am. Chem. Soc. 1993, 115 pp. 10487-10491.

Sofia Svedhem, et al., Synthesis of a Series of Oligo (ethylene glycol)-Terminated Alkanethiol Amides Designed to Address Structure and Stability of Biosensing Interfaces, J. Org. Chem., 2001, 66, pp. 4494-4503.

F.R. Pfeiffer, et al., Glycerolipids. III. Stereospecific Syntheses of D- and L-1,2-Diglycerides via Glycerol Carbonates, The Journal of Organic Chemistry, vol. 35, No. 1, Jan. 1970, pp. 221-224.

P. H. Bentley, et al., An Efficient Synthesis of Symmetrical 1,3-Diglycerides, J. Org. Chem., vol. 35, No. 6, 1970, pp. 2082-2083.

Walfred S. Saari, et al., Cyclization-Activated Prodrugs. Basic Carbamates of 4-Hydroxyanisole, J. Med. Chem. 1990, 33, pp. 97-101.

Tohru Fukuyama, et al., 2,4-Dinitrobenzenesulfonamides: A Simple and Practical Method for the Preparation of a Variety of Secondary Amines and Diamines., Tetrahedron Letters, vol. 38, No. 33, pp. 5831-5834, 1997.

Yiyan Chen et al., Synthesis and Properties of ABA Amphiphiles, J. Org. Chem. 1999, 64, pp. 6870-6873.

Hiroe Kishine, et al., Subgenomic replicon derived from a cell line infected with the hepatitis C virus, Biochemical and Biophysical Research Communications, 293, 2002, pp. 993-999.

* cited by examiner

[FIGURE 1]
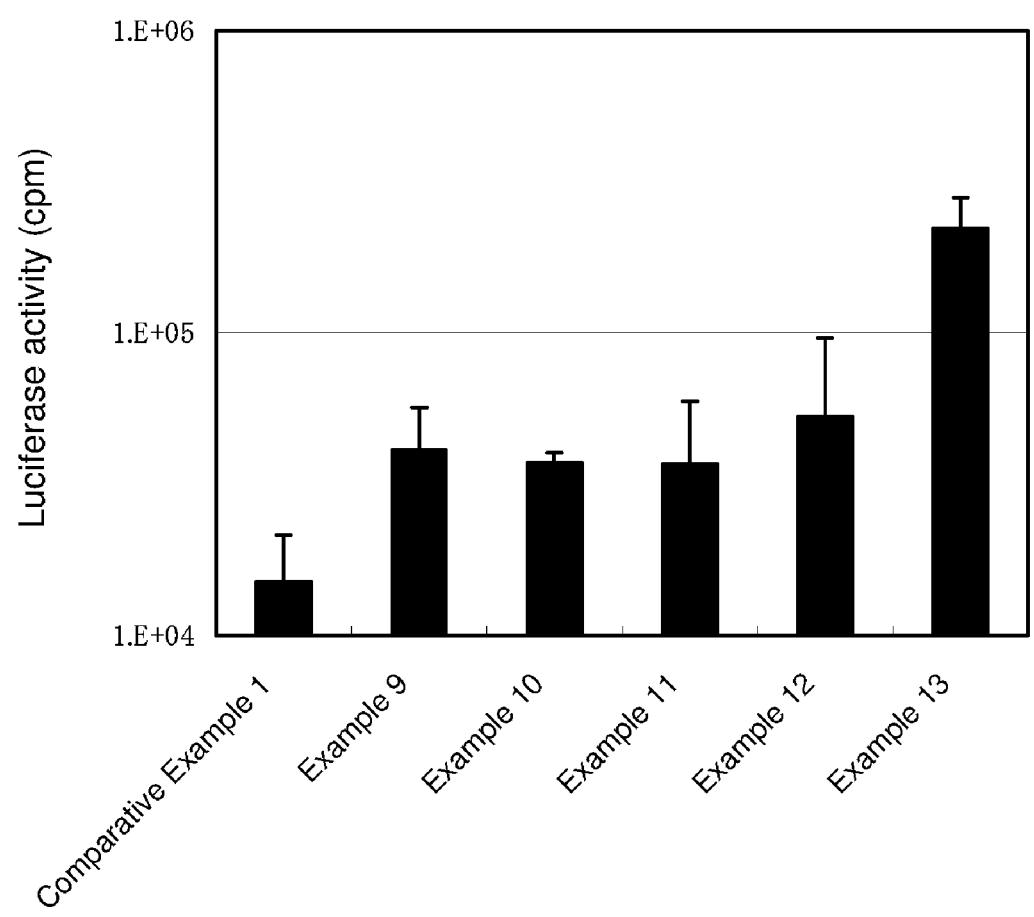

[FIGURE 2]
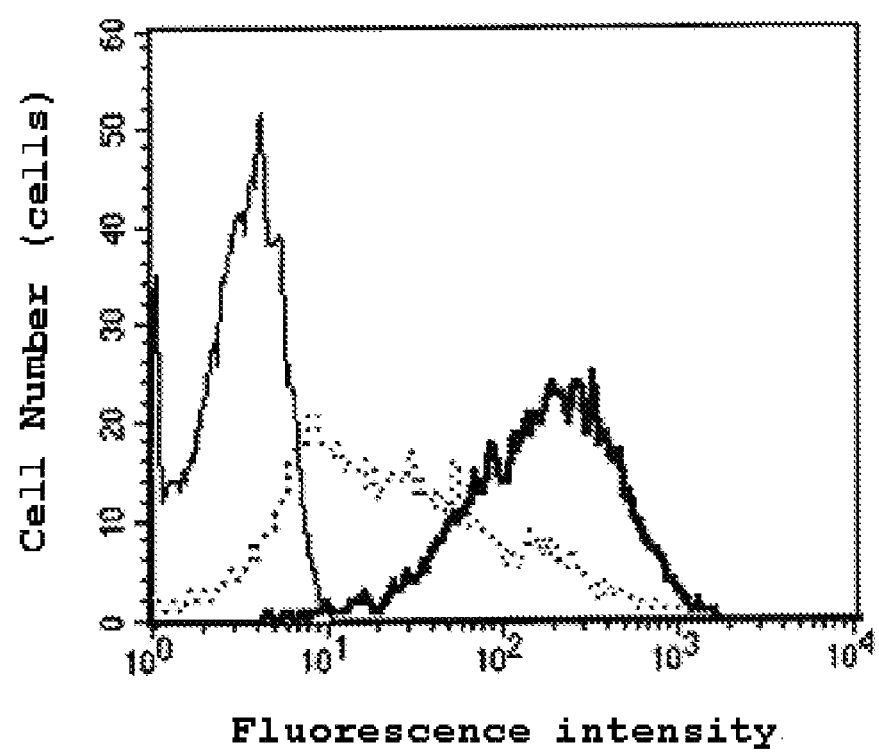

[FIGURE 3]
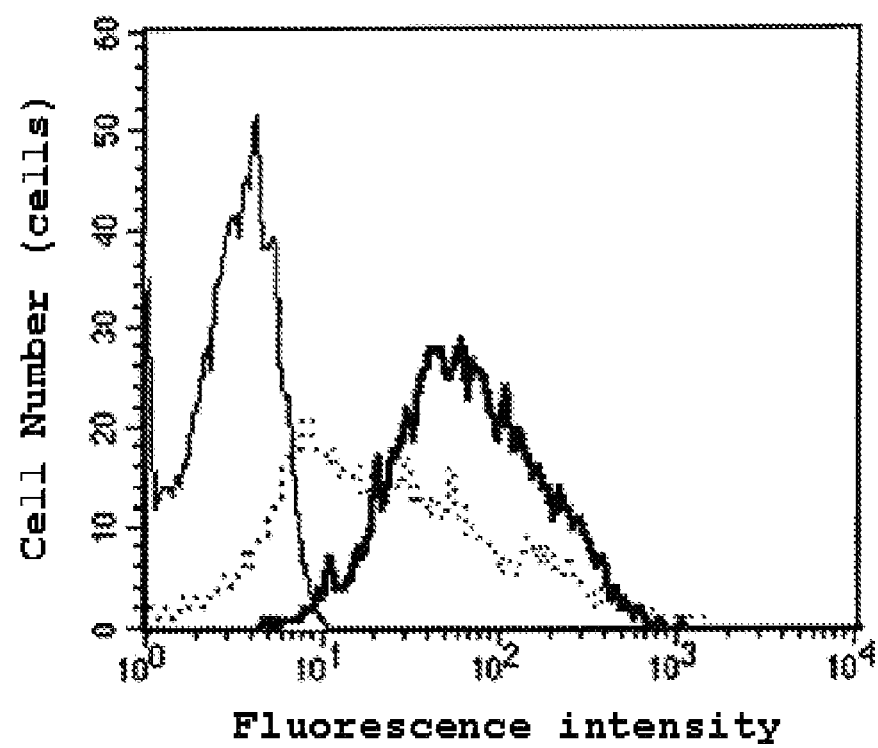

[FIGURE 4]
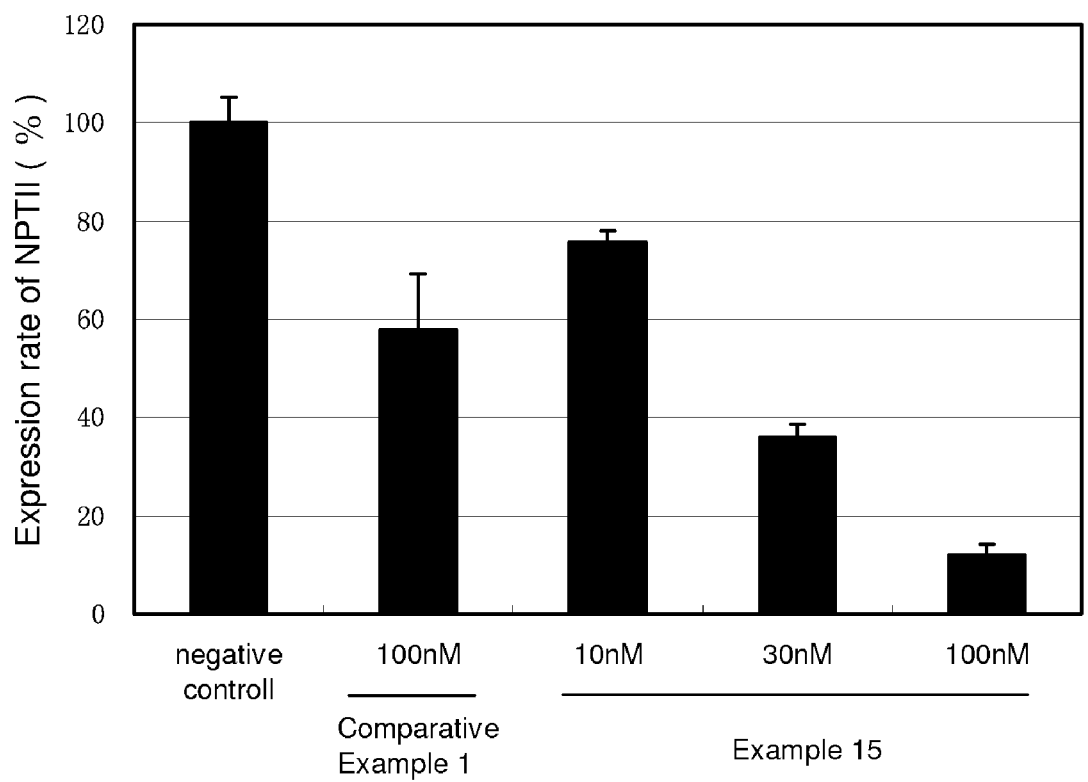

GALACTOSE DERIVATIVE, DRUG CARRIER AND MEDICINAL COMPOSITION

CROSS-REFERENCE TO PRIOR APPLICATIONS

This is a U.S. National Phase Application under 35 U.S.C. §371 of International Patent Application No. PCT/JP2005/015424 filed Aug. 25, 2005, and claims the benefit of Japanese Patent Application No. 2004-246190 filed Aug. 26, 2004, all of which are hereby incorporated by reference in its entirety. The International Application was published in Japanese on Mar. 2, 2006 as WO 2006/022325 A1 under PCT Article 21(2).

FIELD OF THE INVENTION

The present invention relates to a galactose derivative, a drug carrier with liver-targeting property, and a pharmaceutical composition.

BACKGROUND ART

On the surface of hepatocytes, there is a receptor recognizing asialoglycoproteins. The receptor recognizes the galactose residue of asialoglycoproteins, and has a role in the uptake of asialoglycoproteins by hepatocytes (see, for example, M. Spiess, "Biochemistry", 1990, vol. 29, p. 10009-10018).

With such a substrate specificity, it has been studied to improve the liver-targeting of liposomes by way of adding galactose to lipid components of the liposomes. However, none of the studies brought good satisfaction (see, for example, JP-A 1994-271597).

On the other hand, in recent years, utilization of a nucleic acid called short interfering RNA (hereinafter referred to as "siRNA") with RNA interference (hereinafter referred to as "RNAi") as a medicine is noticed, and is investigated actively (see, for example, WO 02/055692 pamphlet, WO 02/055693 pamphlet). siRNA is hard to transfer into cells of a human body if it is administered alone, and it is necessary to administer siRNA by embedding it in a suitable carrier.

DISCLOSURE OF THE INVENTION

Problem to be Solved by the Invention

A main object of the present invention is to provide a novel and useful galactose derivative, a drug carrier comprising the galactose derivative as an essential component, and a pharmaceutical composition comprising the drug carrier including a medicine.

Means to Solve the Problem

The present inventors have conducted extensive research to find that a drug carrier of which one of the components is a galactose derivative made up of galactose, a suitable spacer and a certain lipid makes a significant improvement in the liver-targeting, and have accomplished the present invention.

The present invention can include, for example, inventions illustrated in the following items 1 to 3.

Item 1

A galactose derivative represented by the following general formula (I) (hereinafter referred to as "the derivative of the present invention"),

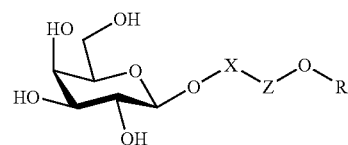
(I)

wherein, X represents the following formula (II) or (III); Z represents the following formula (IV) or (V); R represents the following formula (VI) or (VII);

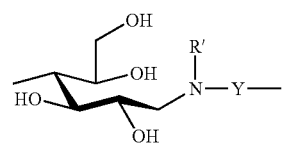
(II)

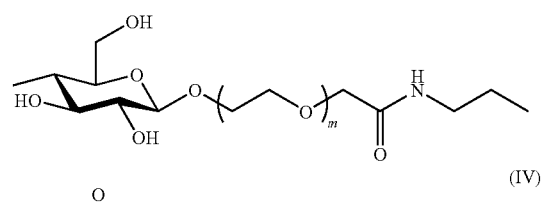
(III)

(IV)

(V)

(VI)

(VII)

Y represents the following formula (VIII) or (IX); R' represents hydrogen or an alkyl having 1 to 10 optionally substituted carbon atoms; R" represents a saturated or unsaturated aliphatic hydrocarbon group having 10 to 30 carbon atoms, or a saturated or unsaturated fatty acid residue having 10 to 30 carbon atoms;

(VIII)

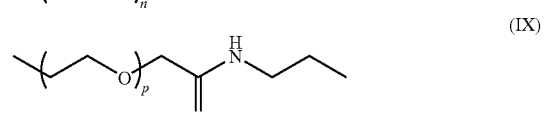
(IX)

and each of m, n and p independently represents an integer from 0 to 50, excluding the following galactose derivatives:

(1) 1,2-dioleoyl-sn-glycerol-3-phosphatidyl-N-(1-deoxylactito-1-yl)ethanolamine,
(2) galactose derivatives in which X is formula (II), Y is formula (VIII), Z is formula (IV), and R is formula (VII) in the general formula (I),
(3) galactose derivatives in which X is formula (II), Y is formula (IX), Z is formula (IV), and R is formula (VII) in the general formula (I), and
(4) galactose derivatives in which X is formula (III), Z is formula (IV), and R is formula (VII) in the general formula (I).

Item 2

A drug carrier which comprises a galactose derivative represented by the following general formula (I) and a cationic lipid (hereinafter referred to as "the carrier of the present invention"),

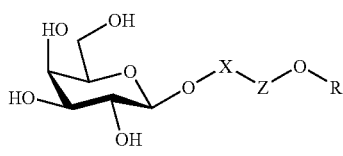
(I)

wherein, X represents the following formula (II) or (III); Z represents the following formula (IV) or (V); R represents the following formula (VI) or (VII);

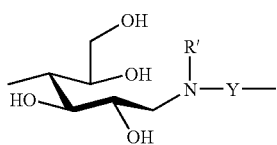
(II)

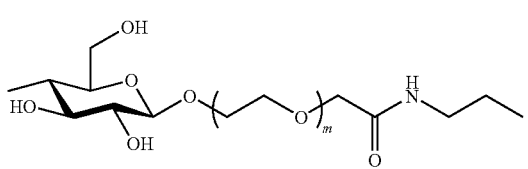
(III)

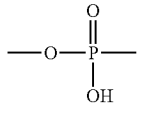
(IV)

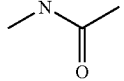
(V)

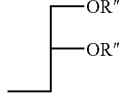
(VI)

(VII)

Y represents the following formula (VIII) or (IX); R' represents hydrogen or an alkyl having 1 to 10 optionally substituted carbon atoms; R" represents a saturated or unsaturated aliphatic hydrocarbon group having 10 to 30 carbon atoms, or a saturated or unsaturated fatty acid residue having 10 to 30 carbon atoms;

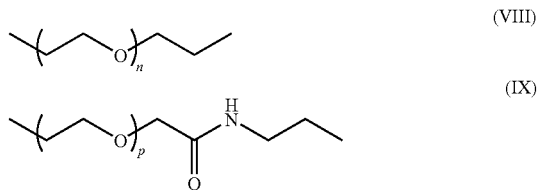
(VIII)

(IX)

and each of m, n and p independently represents an integer from 0 to 50, excluding the following galactose derivatives:
(1) galactose derivatives in which X is formula (II), Y is formula (VIII), Z is formula (IV), and R is formula (VII) in the general formula (I),
(2) galactose derivatives in which X is formula (II), Y is formula (IX), Z is formula (IV), and R is formula (VII) in the general formula (I), and
(3) galactose derivatives in which X is formula (III), Z is formula (IV), and R is formula (VII) in the general formula (I).

Item 3

A pharmaceutical composition which comprises the drug carrier of the above item 2 including a medicine (hereinafter referred to as "the composition of the present invention").

In the present invention, an alkyl having 1 to 10 carbon atoms according to R' is not particularly limited to the form of straight or branched chain, but can include, for example, methyl, ethyl, n-propyl, isopropyl and isobutyl. Among them, the alkyl having 1 to 4 carbon atoms is preferable, and methyl and ethyl are particularly preferable. Examples of the substituted alkyl can include alkoxy and alkyl halide. Specific examples of the alkoxy can include methoxy and ethoxy. The alkyl moiety of the alkyl halide is defined as the same as the above alkyl. In addition, examples of the halogen moiety of the alkyl halide can include fluorine, chlorine and bromine. More particularly, the alkyl halide can include methyl chloride, ethyl chloride and methyl fluoride.

Examples of the saturated aliphatic hydrocarbon group having 10 to 30 carbon atoms according to R" can include capryl, lauryl, myristyl, palmityl and stearyl. Among them, the saturated aliphatic hydrocarbon group having 10 to 20 carbon atoms is preferable, and stearyl is particularly preferable. In addition, examples of the unsaturated aliphatic hydrocarbon group having 10 to 30 carbon atoms can include oleyl, linoleyl and arachidonyl. Among them, the unsaturated aliphatic hydrocarbon group having 10 to 20 carbon atoms is preferable, and oleyl is particularly preferable. Examples of the saturated fatty acid residue having 10 to 30 carbon atoms can include caproyl, lauroyl, myristoyl, palmitoyl and stearoyl. Among them, the saturated fatty acid residue having 10 to 20 carbon atoms is preferable, and stearoyl is particularly preferable. Examples of the unsaturated fatty acid residue having 10 to 30 carbon atoms can include oleoyl, linoleoyl and arachidonoyl. Among them, oleoyl is particularly preferable.

Each of m, n and p may suitably be an integer from 0 to 50 independently, preferably an integer from 0 to 20, and more preferably an integer from 0 to 10.

Examples of the preferred derivative of the present invention can include the following galactose derivatives (1) to (8):

(1) 2-O-{2-N-(1-deoxylactito-1-yl)aminoethyl}carbamoyl-1,3-O-dioleoyl glycerol,
(2) L-α-dioleoyl phosphatidyl{14-N-(1-deoxylactito-1-yl)amino-3,6,9,12-tetraoxa}tetra decanol,
(3) L-α-dioleoyl phosphatidyl-N-{14-(β-1-lactosyloxy)-3,6,9,12-tetraoxa tetradecoxy acetyl}ethanolamine,
(4) 2-O-[2-N-{14-(β-1-lactosyloxy)-3,6,9,12-tetraoxa tetradecoxy acetyl}aminoethyl]carbamoyl-1,3-dioleoyl glycerol,
(5) L-α-dioleoylphosphatidyl{11-N-(1-deoxylactito-1-yl)amino-3,6,9-trioxa}undecanol,
(6) L-α-dioleoyl phosphatidyl{29-N-(1-deoxylactito-1-yl)amino-3,6,9,12,15,18,21,24,27-nonaoxa}oxanonacosanol,
(7) 2-O-[2-{N-(1-deoxylactito-1-yl)-N-ethyl}aminoethyl]carbamoyl-1,3-O-dioleoyl glycerol, and
(8) 2-O-{11-N-(1-deoxylactito-1-yl)amino-3,6,9-trioxaundecyl}carbamoyl-1,3-O-dioleoyl glycerol.

BRIEF DESCRIPTION OF DRAWINGS

FIG. 1 shows the expression efficiency of luciferase. The vertical axis indicates the luciferase activity, and the horizontal axis indicates Examples of the composition examined.

FIG. 2 shows the distribution of fluorescence intensity. The vertical axis indicates the cell number, and the horizontal axis indicates fluorescence intensity. The broken line indicates the distribution of fluorescence intensity of the comparative composition, and the bold solid line indicates the distribution of fluorescence intensity of the composition including the carrier of the present invention according to Example 11. In addition, the fine solid line indicates the distribution of fluorescence intensity of the negative control.

FIG. 3 shows the distribution of fluorescence intensity. The vertical axis indicates the cell number, and the horizontal axis indicates fluorescence intensity. The broken line indicates the distribution of fluorescence intensity of the comparative composition, and the bold solid line indicates the distribution of fluorescence intensity of the composition including the carrier of the present invention according to Example 14. In addition, the fine solid line indicates the distribution of fluorescence intensity of the negative control.

FIG. 4 shows the inhibitory activity on the replication of hepatitis C virus (herein after referred to as "HCV") replicon. The vertical axis indicates the expression rate of neomycin phosphotransferase II (herein after referred to as "NPTII"), and the horizontal axis indicates Examples of the composition examined and the concentration of an oligo RNA in the examined composition.

BEST MODE FOR CARRYING OUT THE INVENTION

I. Process for Producing the Derivative of the Present Invention

1. Process for Producing the Derivative (Ia) of the Present Invention Wherein X is the Above Formula (II)

(a) The derivative (Ia) of the present invention wherein X is the above formula (II) can be produced by reacting D-(+)-lactose (1) with an amine derivative represented by the following general formula (2) in the presence of a reducing agent under acidic condition after dissolving them in a suitable solvent. The solvent which may be used in the reaction is not specifically limited unless it is involved in the reaction, but can include, for example, water, alcohols (e.g., methanol, ethanol and isopropyl alcohol), halogenated hydrocarbons (e.g., dichloromethane, dichloroethane and chloroform) and solvent mixtures thereof. Examples of the acid used to make an acidic condition can include acetic acid and hydrochloric acid. Examples of the reducing agent can include sodium borohydride and sodium cyanoborohydride. The reaction temperature is preferably in the range from 0 to 80° C. In addition, the reaction time varies depending on the kind of raw materials used and the reaction temperature applied, but is preferably in the range from 1 to 100 hours.

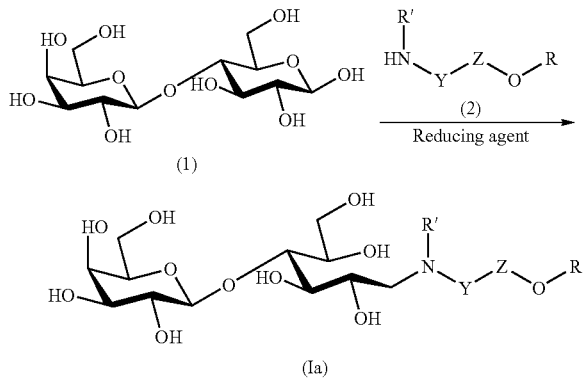

(wherein Y, Z, R and R' are defined as the same as the above-mentioned.)

(b) The derivative (Ia-2) of the present invention of the above general formula (Ia) wherein R' is not hydrogen can also be produced by reacting the derivative (Ia-1) of the present invention wherein R' is hydrogen, which can be produced by the above method (a), with an aldehyde or the ketone represented by the following general formula (3) in the presence of a reducing agent under acidic condition after dissolving them in a suitable solvent. The solvent which may be used is not specifically limited unless it is involved in the reaction, but can include, for example, water, alcohols (e.g., methanol, ethanol and isopropyl alcohol), halogenated hydrocarbons (e.g., dichloromethane, dichloroethane and chloroform) and solvent mixtures thereof. Examples of the acid used to make the acidic condition can include acetic acid and hydrochloric acid. Examples of the reducing agent can include sodium borohydride and sodium cyanoborohydride. The reaction temperature is preferably in the range from 0 to 80° C. In addition, the reaction time varies depending on the kind of raw materials used and the reaction temperature applied, but is preferably in the range from 1 to 100 hours.

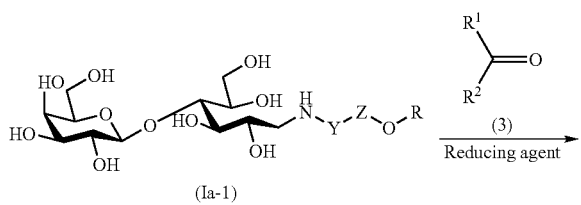

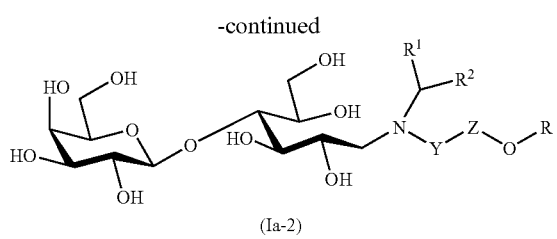

(Ia-2)

(wherein Y, Z and R are defined as the same as the above-mentioned.)

Wherein, $R^1$ and $R^2$ represent the same or different hydrogen or an alkyl having 1 to 9 optionally substituted carbon atoms. The alkyl having 1 to 9 carbon atoms is not particularly limited to the form of straight or branched chain, and can include, for example, methyl, ethyl, n-propyl, isopropyl and isobutyl. Among them, the alkyl having 1 to 3 carbon atoms is preferable, and methyl and ethyl are particularly preferable. In addition, examples of the substituent of the alkyl can include alkoxy (e.g., methoxy and ethoxy) and halogen (e.g., fluorine, chlorine and bromine).

2. Process for Producing the Derivative (Ib) of the Present Invention Wherein X is the Above Formula (III)

(a) The derivative (Ib) of the present invention wherein X is the above formula (III) can be produced by reacting a carboxylic acid represented by the following general formula (4) with an amine derivative (2f) of the above general formula (2) wherein Y is the above formula (VIII) and n thereof is 0 in the presence of a condensing agent after dissolving them in a suitable solvent. The solvent which may be used is not specifically limited unless it is involved in the reaction, but can include, for example, halogenated hydrocarbons (e.g., dichloromethane, chloroform, carbon tetrachloride and 1,2-dichloroethane), acetonitrile, dimethylformamide and solvent mixtures thereof. Examples of the condensing agent can include N,N'-dicyclohexylcarbodiimide, 1-ethyl-3-(3-dimethylaminopropyl)carbodiimide and 1-hydroxybenzotriazole. The reaction temperature is preferably in the range from 0 to 30° C. In addition, the reaction time varies depending on the kind of raw materials used and the reaction temperature applied, but is preferably in the range from 1 to 30 hours.

3. Process for Producing the Amine Derivative Represented by the Above General Formula (2) which is a Raw Material of the Derivative (Ia) of the Present Invention (a) The amine derivative (2a) of the above general formula (2) wherein Y is the above formula (VIII), Z is the above formula (IV) and R is the above formula (VI) can be produced by using the aminoalcohol represented by the following general formula (6) and phospholipase D in accordance with a method described in the document (J. Am. Chem. Soc., 1993, 115, p. 10487-10491).

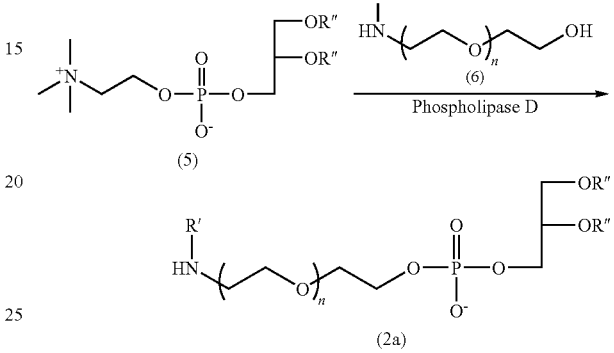

(wherein R', R" and n are defined as the same as the above-mentioned.)

(b) The amine derivative (2b) of the above general formula (2) wherein R' is hydrogen, Y is the above formula (VIII) and Z is the above formula (V) can be produced by dissolving an alcohol represented by the following general formula (7) in a suitable solvent, reacting the alcohol with a suitable acylating agent to obtain an activator, and then reacting the obtained activator with an amine derivative represented by the following general formula (8) to obtain the compound represented by the following general formula (9), followed by removing $R^3$ in a conventional method. The solvent which may be used is not specifically limited unless it is involved in the reaction, but can include, for example, organic amines (e.g., pyridine, picoline and collidine), dimethylformamide and solvent mixtures thereof. Examples of the acylating agent can include N,N'-carbon-

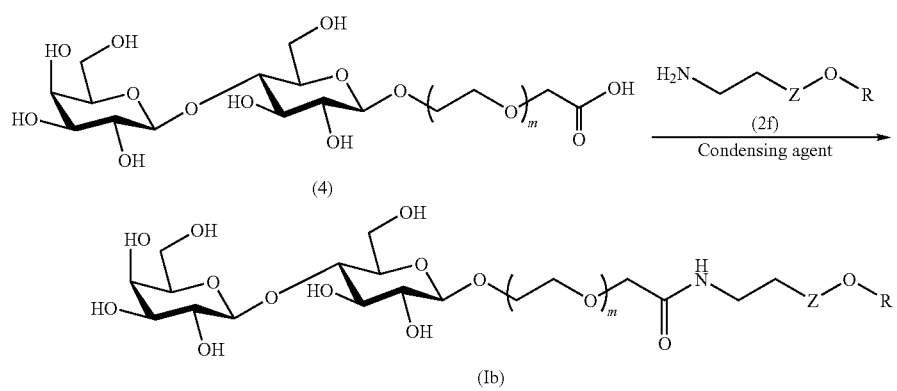

(wherein Z, R and m are defined as the same as the above-mentioned.)

yldiimidazole and chlorocarbonic acid phenyl. The reaction temperature is preferably in the range from 0 to 100°

C. In addition, the reaction time varies depending on the kind of raw materials used and the reaction temperature applied, but is preferably in the range from 1 to 30 hours. The removal of $R^3$ can be performed by treating with an acid (e.g., trifluoroacetic acid, acetic acid and hydrochloric acid), or carrying out catalytic reduction in accordance with a conventional method.

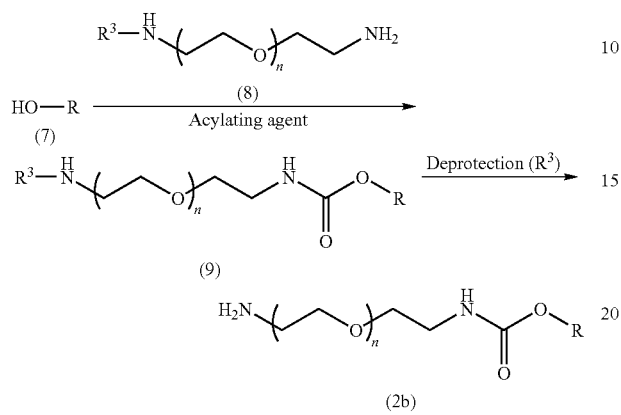

(wherein R and n are defined as the same as the above-mentioned.)

Wherein, $R^3$ represents a protecting group of the amino group. The protecting group is not specifically limited, but can include, for example, tert-butyloxycarbonyl and benzyloxycarbonyl. Among them, tert-butyloxycarbonyl is particularly preferable.

(c) The amine derivative (2c) of the above general formula (2) wherein R' is not hydrogen, Y is the above formula (VIII) and Z is the above formula (V) can be produced by reacting an alcohol represented by the following general formula (7) with an amine derivative represented by the following general formula (10) in the presence of an acylating agent after dissolving them in as suitable solvent. The solvent which may be used is not specifically limited unless it is involved in the reaction, but can include, for example, organic amines (e.g., pyridine, picoline and collidine), dimethylformamide and solvent mixtures thereof. Examples of the acylating agent can include N,N'-carbonyldiimidazole and chlorocarbonic acid phenyl. The reaction temperature is preferably in the range from 0 to 100° C. In addition, the reaction time varies depending on the kind of raw materials used and the reaction temperature applied, but is preferably in the range from 1 to 30 hours.

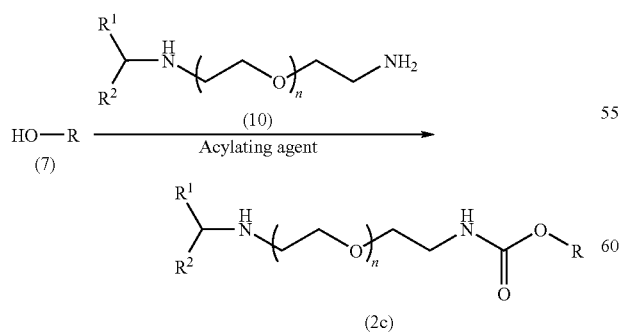

(wherein R, $R^1$, $R^2$ and n are defined as the same as the above-mentioned.)

(d) The amine derivative (2d) of the above formula (2) wherein R' is hydrogen, Y is the above formula (IX) and p is 1 or more can be produced by obtaining a compound represented by the following general formula (16) with an ethylene glycol derivative represented by the following general formula (11) in accordance with a method described in the document (J. Org. Chem., 2001, 66, p. 4494-4503), removing $R^4$, and then reacting the compound in which $R^4$ is removed with an amine derivative represented by the above general formula (2f) in the presence of a suitable condensing agent, followed by removing $R^3$ in a conventional method. Examples of the condensing agent can include N,N'-dicyclohexylcarbodiimide, 1-ethyl-3-(3-dimethylaminopropyl) carbodiimide and 1-hydroxybenzotriazole. The introduction of the protecting group can be performed by reacting di-tert-butyl dicarbonate or the like in a solvent such as tetrahydrofuran in accordance with a conventional method, for example. The removal of $R^4$ can be performed by treating with aqueous sodium hydroxide, sodium methylate or the like in an alcohol such as methanol, or carrying out catalytic reduction in accordance with a conventional method.

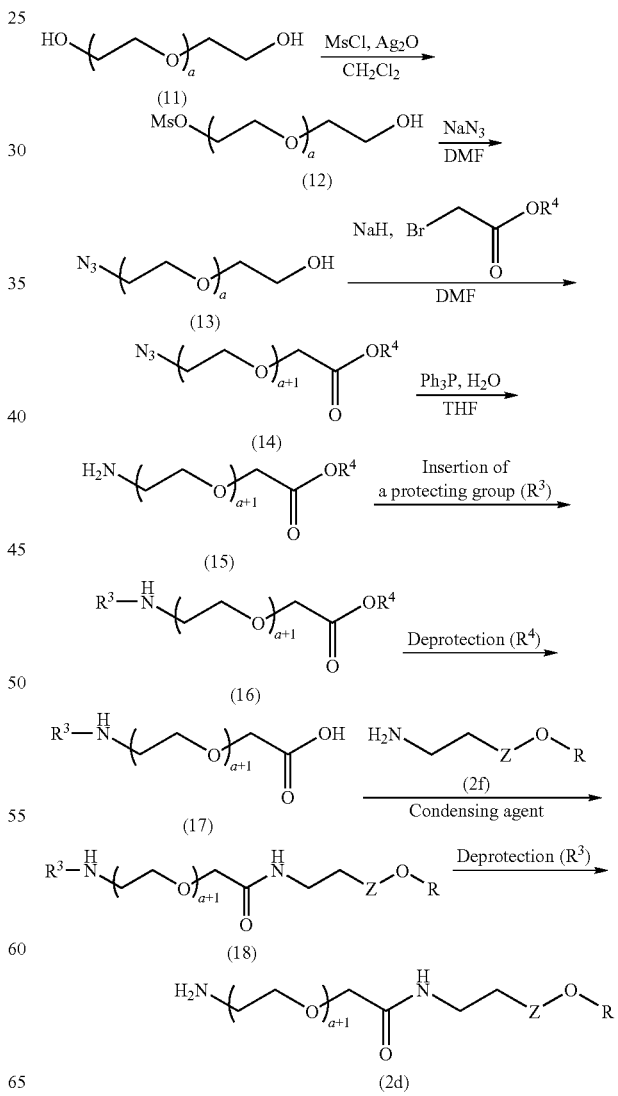

(wherein Z, R and $R^3$ are defined as the same as the above-mentioned.)

Wherein, a represents an integer from 0 to 49. In addition, $R^4$ represents an optionally substituted alkyl. Examples of the alkyl of $R^4$ can include a straight or branched alkyl having 1 to 7 carbon atoms. More particularly, the alkyl can include methyl, ethyl, tert-butyl, isopropyl and heptyl. In addition, examples of the substituent of the alkyl can include alkoxy (e.g., methoxy and ethoxy) and nitryl (e.g., cyano). Further, Ms represents methanesulphonyl.

(e) The amine derivative (2e) of the above formula (2) wherein R' is hydrogen, Y is the above formula (IX) and p is 0 can be produced by reacting with a glycine derivative represented by the following general formula (19) instead of the compound represented by the above general formula (17) in the process for producing the above amine derivative (2d) in the presence of a suitable condensing agent, followed by removing $R^3$ in a conventional method. Examples of the condensing agent can include N,N'-dicyclohexylcarbodiimide, 1-ethyl-3-(3-dimethylaminopropyl)carbodiimide and 1-hydroxybenzotriazole.

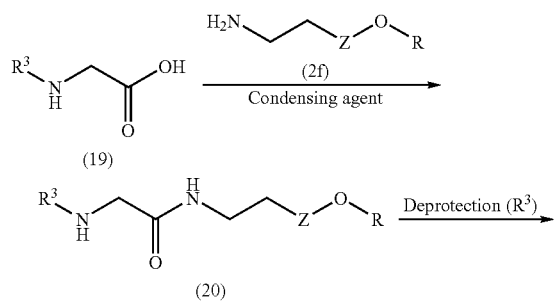

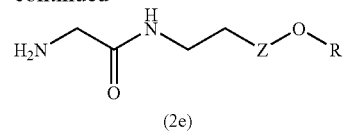

(wherein Z, R and $R^3$ are defined as the same as the above-mentioned.)

4. Process for Producing the Carboxylic Acid Represented by the Above General Formula (4) which is a Raw Material of the Derivative (Ib) of the Present Invention The carboxylic acid represented by the above general formula (4) can be produced by reacting a sugar, in which hydroxyl group is acylated, represented by the following general formula (21) with an alcohol derivative represented by the following general formula (22) in the presence of an acid catalyst after dissolving them in a suitable solvent, followed by removing $R^4$ and $R^5$. The solvent which may be used is not specifically limited unless it is involved in the reaction, but can include, for example, halogenated hydrocarbons (e.g., dichloromethane, dichloroethane and chloroform), ethers (e.g., tetrahydrofuran, diethyl ether and 1,4-dioxane) and solvent mixtures thereof. Examples of the acid catalyst can include trifluoride.diethylether complex and trimethylsilyl trifluoromethanesulfonate. The reaction temperature is preferably in the range from 0 to 30° C. In addition, the reaction time varies depending on the kind of raw materials used and the reaction temperature applied, but is preferably in the range from 1 to 30 hours. The removals of $R^4$ and $R^5$ can be performed by adding sodium methylate in methanol in accordance with a conventional method, and then $R^4$ is not removed under this condition, subsequently by treating with an acid (e.g., trifluoroacetic acid, acetic acid and hydrochloric acid) or carrying out catalytic reduction then subsequently.

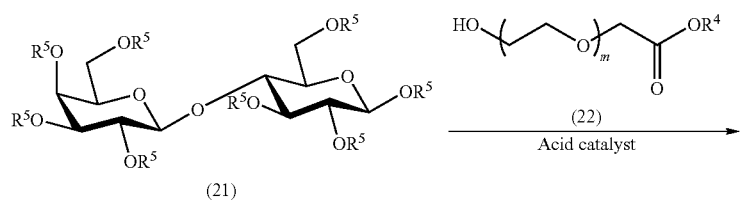

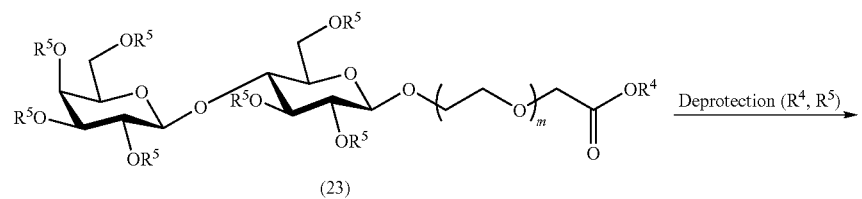

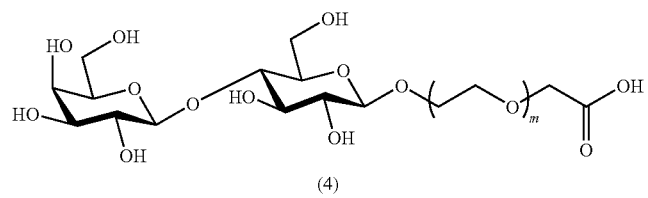

(wherein $R^4$ and m are defined as the same as the above-mentioned.)

Wherein, $R^5$ represents an optionally substituted acyl. The acyl of $R^5$ is not specifically limited, but can include, for example, a straight or branched alkanoyl having 1 to 6 carbon atoms (more particularly, acetyl, isobutyryl and pivaloyl) and aroyl having 7 to 13 carbon atoms (more particularly, benzoyl, toluoyl and 2,4,6-trimethyl benzoyl). In addition, examples of the substituents of the acyl can include alkoxy (e.g., methoxy) halogen (e.g., chlorine and fluorine).

5. Process for Producing the Aminoalcohol Represented by the Above General Formula (6) which is a Raw Material of the Amine Derivative (2a)

The aminoalcohol (6a) of the above general formula (6) wherein R' is hydrogen can be produced by using the azido derivative (13a) of the above general formula (13) wherein a is n in accordance with a method described in the document (J. Org. Chem., 2001, 66, p. 4494-4503). In addition, the aminoalcohol (6b) of the above general formula (6) wherein R' is not hydrogen can also be produced by using the aminoalcohol (6a) of the above general formula (6) wherein R' is hydrogen and an aldehyde or a ketone represented by the above general formula (3) in the same manner as in the above process for producing the derivative of the present invention represented by the above general formula (Ia-2). Examples of the reducing agent can include sodium borohydride and sodium cyanoborohydride.

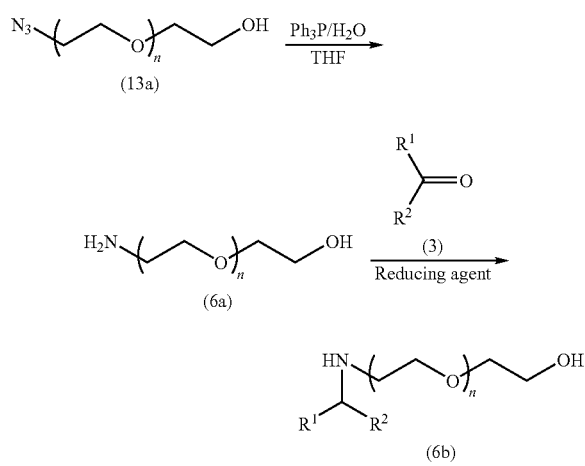

(wherein $R^1$, $R^2$ and n are defined as the same as the above-mentioned.)

6. Process for Producing the Alcohol Represented by the Above General Formula (7) which is a Raw Material of the Amine Derivatives (2b) and (2c)

(a) The alcohol (7a) of the above general formula (7) wherein R is the above formula (VI) can be produced by using 2,2-dimethyl-1,3-dioxolane-4-methanol (24) in accordance with a method described in the document (J. Org. Chem., 1970, 35, p. 221-224) Examples of the base can include organic amines such as pyridine, collidine and triethylamine.

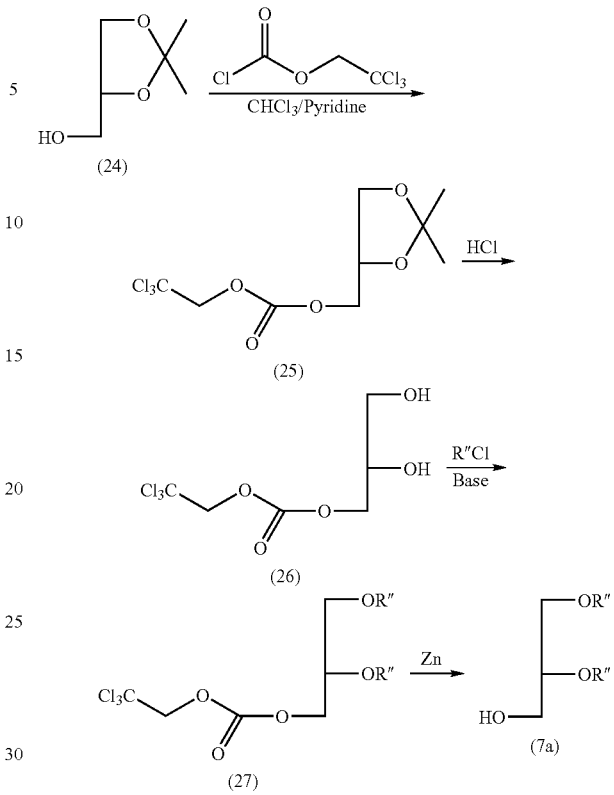

(wherein R" is defined as the same as the above-mentioned.)

(b) The alcohol (7b) of the above general formula (7) wherein R is the above formula (VII) can be produced by using dimeric dihydroxyacetone (28) in accordance with a method described in the document (J. Org. Chem., 1970, 35, p. 2082-2083). Examples of the condensing agent can include N,N'-dicyclohexylcarbodiimide, 1-ethyl-3-(3-dimethylaminopropyl)carbodiimide and 1-hydroxybenzotriazole. Examples of the reducing agent can include, for example, sodium borohydride.

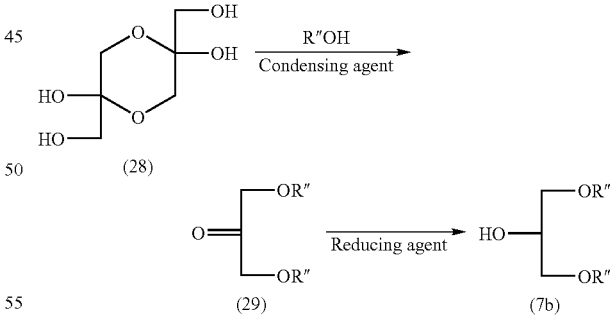

(wherein R" is defined as the same as the above-mentioned.)

7. Process for Producing the Amine Derivative Represented by the Above General Formula (8) which is a Raw Material of the Amine Derivative (2b)

The amine derivative represented by the above general formula (8) can be produced by using the ethylene glycol derivative (11a) of the above general formula (11) wherein a is n in accordance with a method described in the document (J. Org. Chem., 2001, 66, p. 4494-4503 and J. Med. Chem., 1990, 33, p. 97-101). The introduction of the protecting group can be performed by reacting with di-tert-butyl dicarbonate or the like in a solvent such as tetrahydrofuran in accordance with a conventional method, for example.

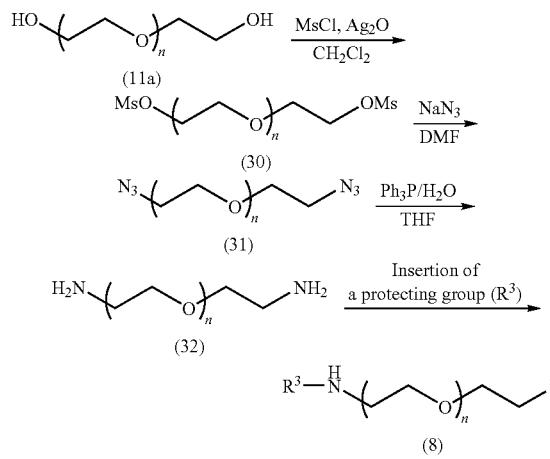

(wherein $R^3$, n and Ms are defined as the same as the above-mentioned.)

8. Process for Producing the Amine Derivative Represented by the Above General Formula (10) which is a Raw Material of the Amine Derivative (2c)

The amine derivative represented by the above general formula (10) can be produced by using the aminoalcohol represented by the above general formula (6a) in accordance with a method described in the document (Tetraedron Letters, 1997, 38, p. 5831-5834). Examples of the reducing agent can include sodium borohydride and sodium cyanoborohydride. The deprotection can be performed by carrying out catalytic reduction in accordance with a conventional method, for example.

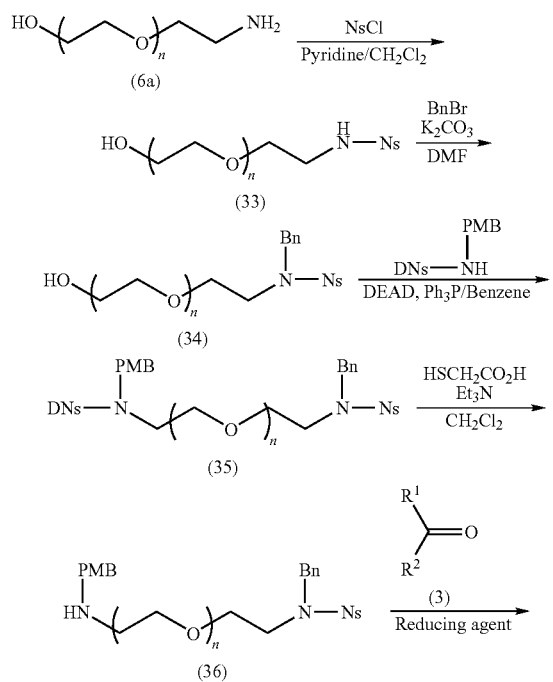

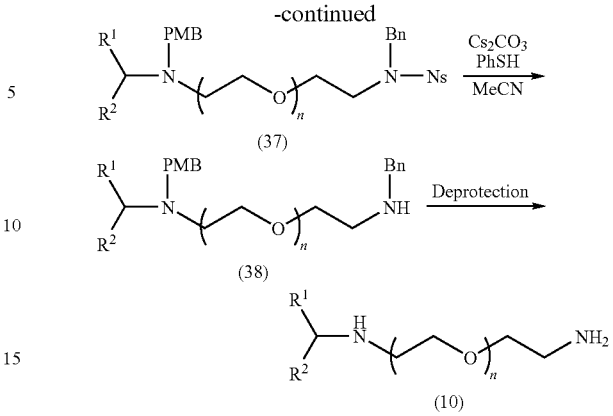

(wherein $R^1$, $R^2$ and n are defined as the same as the above-mentioned.)

Wherein, Ns, Bn, DNs and PMB represent 2-nitrobenzene sulfonyl, benzil, 2,4-dinitrobenzene sulfonyl, and p-methoxybenzyl respectively.

9. Process for Producing the Alcohol Derivative Represented by the Above General Formula (22) which is a Raw Material of the Carboxylic Acid Represented by the Above General Formula (4)

The alcohol derivative (22a) of the above general formula (22) wherein m is 1 or more can be produced by using the ethylene glycol derivative represented by the above general formula (11) in accordance with a method described in the document (J. Org. Chem., 2001, 66, p. 4494-4503). The removal of trityl can be performed by treating with an acid (e.g., trifluoroacetic acid, an acetic acid and hydrochloric acid) in accordance with a conventional method, for example. Meanwhile, the alcohol derivative (22b) of the above general formula (22) wherein m is 0 is commercially available.

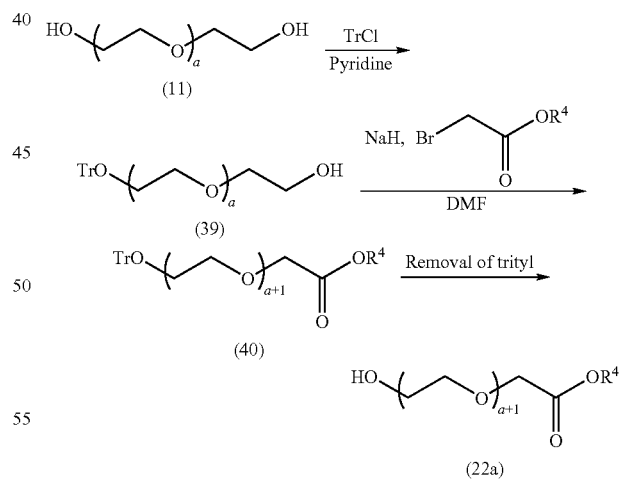

(wherein $R^4$ and a are defined as the same as the above-mentioned.)

Wherein, Tr represents trityl.

10. Process for Producing the Ethylene Glycol Derivative (11c) of the Above General Formula (11) Wherein a is 8 or More The ethylene glycol derivative (11c) of the above general formula (11) wherein a is 8 or more can be produced by using the ethylene glycol derivative (11b) of the above general formula (11) wherein a is b and the ethylene glycol derivative (39a) of the above general formula (39) wherein a is c in accordance with a method described in the document (J. Org. Chem., 1999, 64, p. 6870-6873). Meanwhile, the ethylene glycol derivative (11d) of the above general formula (11) wherein a is 7 or less is commercially available.

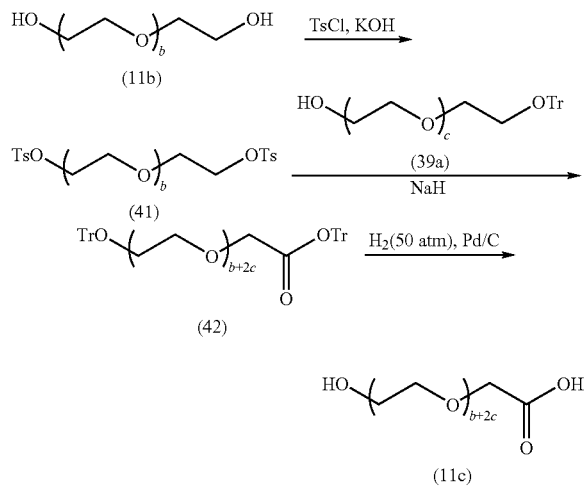

(wherein Tr is defined as the same as the above-mentioned.)

Wherein, b and c represent an integer from 1 to 48, and 1 to 24, respectively. Meanwhile, "b+2c" is a and represents an integer from 8 to 50. In addition, Ts represents p-toluenesulfonyl.

11. Process for Producing the Azido Derivative (13c) of the Above General Formula (13) Wherein a is 8 or More The azido derivative (13c) of the above general formula (13) wherein a is 8 or more can be produced by using the ethylene glycol derivative (39b) of the above general formula (39) wherein m is d and the azido derivative (13b) of the above general formula (13) wherein a is e in accordance with a method described in the document (J. Org. Chem., 2001, 66, p. 4494-4503).

medicine as described below intracellularly. More particularly, the carrier of the present invention can be in the form of a liposome, a fat emulsion or the like.

The cationic lipid which is an essential component of the carrier of the present invention is not particularly limited insofar as it is pharmaceutically acceptable cationic lipid, but can include, for example, 2-O-(2-diethylaminoethyl)carbamoyl-1,3-O-dioleoyl glycerol, N-{1-(2,3-dioleyloxy)propyl}-N,N,N-trimethylammonium chloride, dimethyl dioctadecyl ammoniumbromide, 1,2-dimyristyloxypropyl-3-dimethyl-hydroxy ethylammonium bromide, N,N$^I$,N$^{II}$,N$^{III}$-tetramethyl-N,N$^I$,N$^{II}$,N$^{III}$-tetrapalmityl spermine and 2,3-dioleyloxy-N-{2-(spermine carboxamido)ethyl}-N,N-dimethyl-1-propanaminium trifluoroacetate. These can be used alone or as a mixture of two or more thereof. Among them, 2-O-(2-diethylaminoethyl) carbamoyl-1,3-O-dioleoyl glycerol is particularly preferable.

The formulating ratio of the derivative of the present invention to the cationic lipid in the carrier of the present invention may suitably be in the range from 0.01 to 10 parts by weight of the derivative to 1 part by weight of the cationic lipid, preferably in the range from 0.05 to 5 parts by weight, and more preferably in the range from 0.5 to 3 parts by weight.

Other than the derivative of the present invention and the cationic lipid which are essential components of the carrier of the present invention, a phospholipid can further be added. The phospholipid is not particularly limited insofar as it is a pharmaceutically acceptable lipid, but can include, for example, phosphatidylcholine, phosphatidylethanolamine, phosphatidylinositol, phosphatidylserine, sphingomyelin and lecithin. These can be used alone or as a mixture of two or more thereof. Among them, egg yolk phosphatidylcholine, egg yolk lecithin and soybean lecithin are particularly preferable.

When the phospholipid is further added, the formulating ratio of the derivative of the present invention to the phospholipid in the carrier of the present invention may suitably be in the range from 0.01 to 100 parts by weight of the derivative to 1 part by weight of the phospholipid, preferably in the range from 0.1 to 10 parts by weight, more preferably in the range from 0.3 to 2 parts by weight. In addition, the sum of the derivative of the present invention and the phospholipid may suitably be in the range from 0.01 to 10 parts by weight to 1

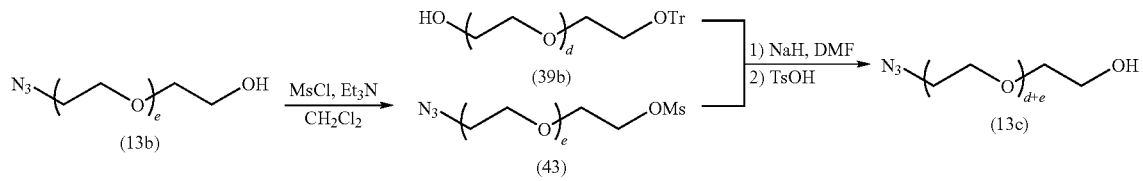

(wherein Ms, Tr and Ts are defined as the same as the above-mentioned.)

Wherein, each of d and e independently represents an integer from 1 to 49. Meanwhile, "d+e" is a and represents an integer from 8 to 50.

II. The Carrier of the Present Invention

The carrier of the present invention includes the derivative of the present invention and a cationic lipid as essential components, and has a property of intracellularly delivering a part by weight of the cationic lipid, preferably in the range from 0.05 to 5 parts by weight, more preferably in the range from 0.5 to 3 parts by weight.

The aqueous dispersion of the carrier of the present invention is prepared by mixing the derivative of the present invention with a cationic lipid and/or a phospholipid, and then dispersing the mixture in an aqueous solution. A machine such as a supersonic dispersing device, an emulsifying dispersion machine and the like may appropriately be used for the dispersion processing.

III. The Composition of the Present Invention

Examples of a medicine used in the composition of the present invention can include water-soluble anionic compounds, antitumor agents, antiviral agents and antibiotics. More particularly, the medicines can include nucleic acid compounds such as double-stranded RNAs, double-stranded DNAs and oligo nucleic acids; acidic saccharides such as heparin sulfate and dextran sulfate; cytokines, second messengers such as cyclic AMP, ATP, IP3, penicillins and cephalosporins; vitamins such as vitamin C and retinols; other known acidic group-containing drugs, interferons ($\alpha,\beta,\gamma$), interleukins (IL-1, IL-2), colony stimulating factor (CSF), tumor necrosis factor (TNF), levamisole, bestatin, retinoic acid, 5-fluorouracil (5-FU), cytosine arabinoside (Ara-C), adenine arabinoside (Ara-A), cisplatin (CDDP), cyclophosphamide, azidothymidine (AZT) and the like.

Examples of the double-stranded RNA can include the followings.

1. Homopolymer-homopolymer complexes
(1) Base-modified
polyinosinic acid-polycytidylic acid,
polyinosinic acid-poly(5-bromo cytidylic acid),
polyinosinic acid-poly(2-thio cytidylic acid),
poly(7-deaza inosinic acid)-polycytidylic acid,
poly(7-deaza inosinic acid)-poly(5-bromo cytidylic acid).
(2) Ribose-modified
poly(2'-azide inosinic acid)-polycytidylic acid.
(3) Phosphate-modified
polyinosinic acid-poly(cytidine-5'-thiophosphate).

2. Homopolymer-copolymer complexes
polyinosinic acid-poly(cytidylic acid-uridine acid),
polyinosinic acid-poly(cytidylic acid-4-thiouridine acid).

3. Synthetic nucleic acid-polycation complexes
polyinosinic acid-polycytidylic acid-poly-L-lysine.

4. Others
polyinosinic acid-poly(1-vinyl cytidylic acid).

The oligo nucleic acid can include an RNA, a DNA and derivatives thereof which have 10 to 50 nucleic acid bases in one molecule, preferably 15 to 30 nucleic acid bases, and more preferably 18 to 25 nucleic acid bases. The oligo nucleic acids can include, for example, an siRNA, an miRNA, an shRNA, an antisense DNA, an antisense RNA, a DNA enzyme, a ribozyme and an aptamer.

The above oligo nucleic acid is not limited to the naturally occurring type, and it is possible to modify at least a part of a nucleotide, such as a sugar and a phosphate backbone constituting the nucleotide, in order to enhance in vivo stability such as a nuclease resistance. In the case of modification, preferable modification may be a modification of 2' position of the sugar, a modification of positions other than 2' position of the sugar, a modification of the phosphate backbone of the oligo nucleic acid, or the like. The modifications of 2' position of the sugar can include a replacement with $OR^6$, $R^6$, $R^7OR^6$, SH, $SR^6$, $NH_2$, $NHR^6$, $N(R^6)_2$, $N_3$, CN, F, Cl, Br, I and the like. Here, $R^6$ represents an alkyl or an aryl, preferably an alkyl having 1 to 6 carbon atoms, and $R^7$ represents an alkylene, preferably an alkylene having 1 to 6 carbon atoms. Products with the modification of the other parts of the sugar can include a 4' thio form and the like. Products with the modification of the phosphate backbone of the oligo nucleic acid can include a phosphorothioate form, a phosphorodithioate form, an alkylphosphonate form, a phosphoroamidate form and the like.

The weight ratio of the carrier of the present invention to the medicine in the composition of the present invention (the carrier of the present invention/the medicine) depends on the type of the medicine, the formulating ratio of the derivative of the present invention to the cationic lipid in the carrier of the present invention and so on, and the ratio may suitably be in the range from 0.01 to 1000, preferably in the range from 10 to 300, and more preferably in the range from 100 to 200. Further, when the included medicine is an oligo nucleic acid, the ratio may suitably be in the range from 0.01 to 100, preferably in the range from 1 to 30, and more preferably in the range from 10 to 20.

In the composition of the present invention, pharmaceutically acceptable additives can be optionally blended besides the carrier of the present invention mentioned above and the medicine. The additives include, for example, emulsifying auxiliary agents (e.g., fatty acids of 6 to 22 carbon atoms and their pharmaceutically acceptable salts, albumin and dextran), stabilizers (e.g., cholesterol and phosphatidic acid), tonicity adjusting agents (e.g., sodium chloride, glucose, maltose, lactose, sucrose and trehalose), pH controllers (e.g., hydrochloric acid, nitric acid, phosphoric acid, acetic acid, sodium hydroxide, potassium hydroxide and triethanolamine). These can be used solely or as a mixture of two or more thereof. The amount of the additives in the composition of the present invention may suitably be 90% by weight or less, preferably 70% by weight or less, and more preferably 50% by weight or less.

The composition of the present invention is prepared by adding a medicine to the aqueous dispersion of the carrier of the present invention and then stirring properly. In addition, the composition of the present invention can be prepared by adding a medicine in the process for producing the carrier of the present invention. It is possible to add the above additives at an appropriate time of the process either before or after the dispersing.

The composition of the present invention can be, for example, a liquid formulation or a lyophilized preparation. In the case of the liquid formulation, the concentration of the carrier of the present invention in the composition of the present invention may suitably be in the range from 0.001 to 25% (w/v), preferably in the range from 0.01 to 5% (w/v), and more preferably in the range from 0.1 to 2% (w/v). The above lyophilized preparation can be prepared by freeze-drying the composition of the present invention in the form of a liquid in a conventional method. For example, after adequately sterilizing the composition of the present invention in the form of a liquid, the composition is dispensed into vial containers each in a predetermined amount, and then the complex is subjected to preliminary freezing at about −40 to −20° C. for about 2 hours, followed by a first drying at about 0 to 10° C. under a reduced pressure and a secondary drying at about 15 to 25° C. under a reduced pressure.

Thereafter, in general, the vials are filled with nitrogen gas and closed with stoppers to give the lyophilized preparations of the composition of the present invention.

The freeze-dried preparation of the composition of the present invention is ordinarily reconstituted by adding thereto an appropriate solution (reconstituting solution) to be used. The reconstituting solution can include water for injection, saline and the other standard infusions. The amount of the reconstituting solution may vary depending on the use and the like, and is not particularly limited, but the appropriate amount may be 0.5 to 2 times the amount of the original liquid formulation before the freeze-drying or not more than 500 mL.

The composition of the present invention may preferably be administrated with an administration unit form, and can be administered by intravenous administration, intra-arterial administration, oral administration, intra-tissue administration, transdermal administration, transmucosal administration, or rectal administration to animals including humans. Particularly, the intravenous administration, the transdermal administration, and the transmucosal administration are preferred. The composition is administered in formulations appropriate for the above-mentioned types of administration, such as various injections, an oral preparation, drops, an inhalant, eye drops, an ointment, a lotion and a suppository.

Although it is desirable to change the dose of the composition of the present invention as a medicine taking into account the kind of medicine, formulation, patient's conditions such as age and body weight, route for administration, and characteristics and seriousness of a disease, the dose is, for example, in the range from 0.01 mg/day/person to 10 g/day/person as a medicine for an adult, and preferably in the range from 0.1 mg/day/person to a several grams/day/person. Further, when a medicine contained in the composition of the present invention is an oligo nucleic acid, the dose is generally in the range from 0.1 mg/day/person to 10 g/day/person as an oligo nucleic acid for an adult, and preferably in the range from 1 mg/day/person to a several grams/day/person. This dose may vary depending also on the type of target disease, administration style and target molecule. Therefore, a lower dose may be adequate in some cases, and a higher dose may be necessary in some cases. In addition, the composition may be administered once or several times a day or at intervals of 1 to several days.

EXAMPLES

The present invention will be illustrated more specifically below by referring to Reference Example, Examples, Comparative Example and Test Examples, which are not intended to limit the invention in any way. The use of these and other examples anywhere in the specification is illustrative only, and in no way limits the scope and meaning of the invention or of any exemplified form. Likewise, the invention is not limited to any particular preferred embodiments described herein. Indeed, modifications and variations of the invention may be apparent to those skilled in the art upon reading this specification, and can be made without departing from its spirit and scope. The invention is therefore to be limited only by the terms of the appended claims, along with the full scope of equivalents to which the claims are entitled.

Reference Example 1

Synthesis of 1,2-dioleoyl-sn-glycerol-3-phosphatidyl-N-(1-deoxylactito-1-yl)ethanolamine 460 mg of L-α-dioleoylphosphatidylethanolamine and 223 mg of lactose monohydrate were dissolved in a mixture of 2 mL of water, 8 mL of methanol and 2 mL of dichloromethane. Subsequently, 1 mL of acetic acid and 78 mg of sodium cyanoborohydride were added, and then the solution was stirred overnight at 65° C. After concentrating the reaction solution, the objective compound was extracted by Bligh-Dyer method (Can. J. Biochem. Physiol., 1959, 37, p. 911 and used hereinafter), and 267 mg of the objective compound was obtained by purifying with silica gel column chromatography.

ESI-Mass (m/z)=1093.1 ([M+Na]$^+$)

Example 1

Synthesis of 2-O-{2-N-(1-deoxylactito-1-yl)aminoethyl}carbamoyl-1,3-O-dioleoylglycerol Step 1. Synthesis of 1,3-dioleoylglycerol 3.8 g of dimeric dihydroxyacetone, 25 g of oleic acid, 20 g of 1-ethyl-3-(3-dimethylaminopropyl) carbodiimide hydrochloric acid and 12.9 g of 4-dimethylaminopyridine were added to 150 mL of dichloromethane, and then the solution was stirred for 4 hours at room temperature. The reaction solution was mixed with 0.5 M potassium dihydrogenphosphate solution and subjected to extraction with dichloromethane, and then the extract washed with water and concentrated under reduced pressure after drying. A powder obtained by adding 1 L of methanol to the residue was collected, and then dried. The powder was dissolved in a mixture of 170 mL of tetrahydrofuran and 17 mL of acetic acid solution, and then 1.7 g of sodium borohydride was gradually added. After stirring for 2 hours at room temperature, the reaction solution was mixed with saturated sodium bicarbonate water, and then subjected to extraction with ethyl acetate. The organic layer was concentrated under reduced pressure after drying. The residue was purified with silica gel column chromatography to obtain 14.5 g of the objective compound.

Step 2. Synthesis of 2-O-(2-aminoethyl)carbamoyl-1,3-O-dioleoylglycerol 3.4 g of 1,3-dioleoylglycerol obtained in above step 1 was dissolved in 30 mL of pyridine, to which 1.7 g of N,N'-carbonyldiimidazole were added, and then the solution was stirred overnight at room temperature. After concentrating the reaction solution under reduced pressure, the residue was dissolved in dichloromethane, and then the solution washed with 5% sodium dihydrogenphosphate. The organic layer was concentrated under reduced pressure after drying. Eight hundred mg of the material thus obtained was dissolved in 3 mL of dimethylformamide, and 358 mg of N-(t-butoxycarbonyl)-1,2-ethylenediamine was added. Then, the solution was stirred at room temperature for 3 hours. The reaction solution was mixed with saturated saline, and then subjected to extraction with ethyl acetate. The organic layer was concentrated under reduced pressure after drying. The residue was dissolved in 8 mL of dichloromethane, to which 2 mL of trifluoroacetic acid was added, and then the solution was stirred at room temperature for 30 minutes. The reaction solution was mixed with saturated sodium bicarbonate water, and then subjected to extraction with ethyl acetate. The organic layer was concentrated under reduced pressure after drying. The residue was purified with silica gel column chromatography to obtain 600 mg of the objective compound.

Step 3. Synthesis of 2-O-{2-N-(1-deoxylactito-1-yl)aminoethyl}carbamoyl-1,3-O-dioleoylglycerol 300 mg of 2-O-(2-aminoethyl)carbamoyl-1,3-O-dioleoylglycerol obtained in the above step 2 and 145 mg of lactose monohydrate were dissolved in a mixture of 1 mL of water, 4 mL of methanol and 1 mL of dichloromethane. Subsequently, 0.3 mL of acetic acid and 53 mg of sodium cyanoborohydride were added, and then the solution was stirred overnight at 65° C. After concentrating the reaction solution, the objective compound was extracted by Bligh-Dyer method, and 247 mg of the objective compound (the derivative of the present invention) was obtained by purifying with silica gel column chromatography.

ESI-Mass (m/z)=1034.0 ([M+H]$^+$)

Example 2

Synthesis of L-α-dioleoylphosphatidyl{14-N-(1-deoxylactito-1-yl)amino-3,6,9,12-tetraoxa}tetradecanol

Step 1. Synthesis of 14-{(methylsulfonyl)oxy}-3,6,9,12-tetraoxatetradecanol 80 mL of dichloromethane was added to 10 g of pentaethyleneglycol and 10.7 g of silver oxide, and then 5.8 g of methanesulfonyl chloride dissolved in 16 ml of dichloromethane was added dropwise. After stirring the reaction solution at room temperature for 2 days, the solution was filtered with a celite, and then the filtrate was concentrated under reduced pressure. The residue was purified with silica gel column chromatography to obtain 7.8 g of the objective compound.

Step 2. Synthesis of 14-azide-3,6,9,12-tetraoxatetradecanol 25 mL of dimethylformamide was added to 7.4 g of 14-{(methylsulfonyl)oxy}-3,6,9,12-tetraoxatetradecanol obtained in the above step 1 and 2.28 g of sodium azide, and then the solution was stirred at 110° C. for 2.5 hours. After concentrating the reaction solution under reduced pressure, the residue was coevaporated with toluene. After suspending the residue in ethyl acetate, insolubles were removed by filtration, and then the filtrate was concentrated under reduced pressure. The residue was purified with silica gel column chromatography to obtain 5.7 g of the objective compound.

Step 3. Synthesis of 14-amino-3,6,9,12-tetraoxatetradecanol 5.6 g of 14-azide-3,6,9,12-tetraoxatetradecanol obtained in the above step 2 was dissolved in 60 mL of methanol, and then the solution was hydrogenated for 4 hours in the presence of 800 mg of 10% palladium/carbon. The reaction solution was filtered, and then the filtrate was concentrated under reduced pressure. The residue was purified with silica gel column chromatography to obtain 2 g of the objective compound.

Step 4. Synthesis of L-α-dioleoylphosphatidyl(14-amino-3,6,9,12-tetraoxa)tetradecanol 25 mL of dichloromethane, 3.5 mL of a buffer solution [sodium acetate (100 mM)—calcium chloride (50 mM) buffer solution (pH 6.5)] and 500 units of phospholipase D were added to 1 g of L-α-dioleoylphosphatidylcholine and 1.9 g of 14-amino-3,6,9,12-tetraoxatetradecanol obtained in the above step 3, and then the solution was stirred overnight at 30° C. After concentrating the dichloromethane layer, the residue was purified with silica gel column chromatography to obtain 705 mg of the objective compound.

Step 5. Synthesis of L-α-dioleoylphosphatidyl{14-N-(1-deoxylactito-1-yl)amino-3,6,9,12-tetraoxa}tetradecanol 400 mg of L-α-dioleoylphosphatidyl(14-amino-3,6,9,12-tetraoxa)tetradecanol obtained in the above step 4 and 172 mg of lactose monohydrate were dissolved in a mixture of 2 mL of water, 10 mL of methanol and 2 mL of dichloromethane. Subsequently, 0.4 mL of acetic acid and 82 mg of sodium cyanoborohydride were added, and then the solution was stirred overnight at 70° C. After concentrating the reaction solution, the objective compound was extracted by Bligh-Dyer method, and 248 mg of the objective compound (the derivative of the present invention) was obtained by purifying with silica gel column chromatography.

ESI-Mass (m/z)=1247.0 ([M+H]$^+$)

Example 3

Synthesis of L-α-dioleoylphosphatidyl-N-{14-(β-1-lactosyloxy)-3,6,9,12-tetraoxatetradecoxyacetyl}ethanolamine

Step 1. Synthesis of 16,16,16-triphenyl-3,6,9,12,15-pentaoxahexadecanol 10 g of pentaethyleneglycol was dissolved in a mixture of 100 mL of acetonitrile and 30 mL of pyridine, to which 11 g of trityl chloride were added at 0° C., and then the solution was stirred overnight at room temperature. The reaction solution was mixed with iced water and subjected to extraction with ethyl acetate, and then the organic layer washed with water and concentrated under reduced pressure after drying. The residue was purified with silica gel column chromatography to obtain 6 g of the objective compound.

Step 2. Synthesis of 16,16,16-triphenyl-3,6,9,12,15-pentaoxahexadecoxybenzyl acetate ester 5.5 g of 16,16,16-triphenyl-3,6,9,12,15-pentaoxahexadecanol obtained in the above step 1 was dissolved in 30 mL of dimethylformamide, and then the solution was added dropwise to a suspension containing 2.3 g of sodium hydride in 100 mL of tetrahydrofuran at 0° C. After stirring at room temperature for 30 minutes, the solution was again cooled at 0° C., and then 3.5 g of bromoacetic acid was added. After stirring at room temperature for 2 hours, the reaction solution was mixed with 10% potassium hydrogen sulfate solution and subjected to extraction with dichloromethane, and then the organic layer washed with water and concentrated under reduced pressure after drying. 1.7 mL of benzyl alcohol, 2.4 g of 1-ethyl-3-(3-dimethylaminopropyl)carbodiimide hydrochloric acid and 144 mg of 4-dimethylaminopyridine were added to the residue, and the solution was stirred overnight at room temperature in 50 mL of dichloromethane. The reaction solution was mixed with saturated sodium bicarbonate water, and then subjected to extraction with ethyl acetate. The organic layer was concentrated under reduced pressure after drying. The residue was purified with silica gel column chromatography to obtain 5.5 g of the objective compound.

Step 3. Synthesis of 14-hydroxyl-3,6,9,12-tetraoxatetradecoxybenzyl acetate ester 5.3 g of 16,16,16-triphenyl-3,6,9,12,15-pentaoxahexadecoxybenzyl acetate ester obtained in the above step 2 was dissolved in 80 mL of dichloromethane, to which 4 mL of trifluoroacetic acid was added, and then the solution was stirred at room temperature for 1 hour. The reaction solution was mixed with saturated sodium bicarbonate water, and then subjected to extraction with ethyl acetate. The organic layer was concentrated under reduced pressure after drying. The residue was purified with silica gel column chromatography to obtain 2 g of the objective compound.

Step 4. Synthesis of 14-(β-1-lactosyloxy)-3,6,9,12-tetraoxatetradecoxybenzyl acetate ester 1.76 g of β-lactoseoctacetate, 1.5 g of 14-hydroxyl-3,6,9,12-tetraoxatetradecoxybenzyl acetate ester obtained in the above step 3 were dissolved in 20 mL of dichloromethane, to which 2.4 mL of trifluoride diethylether complex was added at 0° C., and then the solution was stirred overnight at room temperature. The reaction solution was mixed with saturated sodium bicarbonate water and subjected to extraction with ethyl acetate, and then the extract washed with water. The organic layer was concentrated under reduced pressure after drying. The residue was purified with silica gel column chromatography to obtain 1.1 g of the objective compound.

Step 5. Synthesis of 14-(β-1-lactosyloxy)-3,6,9,12-tetraoxatetradecoxy acetic acid 1 g of 14-(β-1-lactosyloxy)-3,6,9,12-tetraoxatetradecoxy-benzyl acetate ester obtained in the above step 4 was dissolved in 18 mL of methanol, to which 2 mL of 28% sodium methoxide/methanol solution was added, and then the solution was stirred at room temperature for 2 hours. After neutralizing the reaction solution with Amberlite (registered-mark) IRC-50, the solution was filtered, and then the filtrate was concentrated under reduced pressure. The residue was separated with water-ethyl acetate, and then the aqueous layer was lyophilized to obtain 310 mg of the objective compound.

Step 6. Synthesis of L-α-dioleoylphosphatidyl-N-{14-(β-1-lactosyloxy)-3,6,9,12-tetraoxatetradecoxyacetyl}ethanolamine 150 mg of 14-(β-1-lactosyloxy)-3,6,9,12-tetraoxatetradecoxy acetic acid obtained in the above step 5, 360 mg of L-α-dioleoylphosphatidylethanolamine, 139 mg of 1-ethyl-3-(3-dimethylaminopropyl)carbodiimide hydrochloric acid and 33 mg of 1-hydroxybenzotriazole were added to 3 mL of dichloromethane, and then the solution was stirred overnight. After concentrating the reaction solution under reduced pressure, the residue was purified with silica gel column chromatography to obtain 44 mg of the objective compound (the derivative of the present invention)

ESI-Mass (m/z)=1269.2 ([M+Na]$^+$)
ESI-Mass (m/z)=1291.3 ([M+2Na]$^+$)
ESI-Mass (m/z)=1344.9 ([M−H]$^−$)

Example 4

Synthesis of 2-O-[2-N-{14-(β-1-lactosyloxy)-3,6,9,12-tetraoxatetradecoxyacetyl}aminoethyl]carbamoyl-1,3-dioleoylglycerol 228 mg of 2-O-(2-aminoethyl)carbamoyl-1,3-dioleoylglycerol obtained in the step 2 of Example 1, 100 mg of 14-(β-1-lactosyloxy)-3,6,9,12-tetraoxatetradecoxy acetic acid obtained in the step 5 of Example 3, 46 mg of 1-ethyl-3-(3-dimethylaminopropyl)carbodiimide hydrochloric acid and 33 mg of 1-hydroxybenzotriazole were added to 3 mL of dichloromethane, and then the solution was stirred overnight. After concentrating the reaction solution under reduced pressure, the residue was purified with silica gel column chromatography to obtain 65 mg of the objective compound (the derivative of the present invention).

ESI-Mass (m/z)=1232.2 ([M+Na]$^+$)

Example 5

Synthesis of L-α-dioleoyl phosphatidyl{11-N-(1-deoxylactito-1-yl)amino-3,6,9-trioxa}undecanol Step 1. Synthesis of 11-{(methylsulfonyl)oxy}-3,6,9-trioxaundecanol 250 mL of dichloromethane was added to 25 g of tetraethylene glycol and 32.8 g of silver oxide, and then a solution of 17.7 g of methanesulfonyl chloride in 50 ml of dichloromethane was added dropwise. After stirring the reaction solution at room temperature for 2 days, the solution was filtered with a celite, and then the filtrate was concentrated under reduced pressure. The residue was purified with silica gel column chromatography to obtain 24 g of the objective compound.

Step 2. Synthesis of 11-azide-3,6,9-trioxaundecanol 100 mL of dimethylformamide was added to 23.5 g of 11-{(methylsulfonyl)oxy}-3,6,9-trioxaundecanol obtained in the above step 1 and 8.4 g of sodium azide, and then the solution was stirred at 110° C. for 3 hours. After concentrating the reaction solution under reduced pressure, the residue was coevaporated with toluene. After suspending the residue methylacetate, insolubles were removed by filtration, and then the filtrate was concentrated under reduced pressure. The residue was purified with silica gel column chromatography to obtain 18.5 g of the objective compound.

Step 3. Synthesis of 11-amino-3,6,9-trioxaundecanol 3 g of 11-azide-3,6,9-trioxaundecanol obtained in the above step 2 was dissolved in 35 mL of tetrahydrofuran, and then 3.95 mg of triphenyl phosphine was added. After stirring at room temperature for 18 hours, 10 mL of water was added, and then the solution was further stirred overnight. The reaction solution was separated with toluene and water, and then the aqueous layer was lyophilized to obtain 2.4 g of the objective compound.

Step 4. Synthesis of L-α-dioleoylphosphatidyl(11-amino-3,6,9-trioxa)undecanol 25 mL of dichloromethane, 3.5 mL of a buffer solution [sodium acetate (100 mM)—calcium chloride (50 mM) buffer solution (pH 6.5)] and 500 Unit of phospholipase D were added to 1 g of L-α-dioleoylphosphatidylcholine and 1.5 g of 11-amino-3,6,9-trioxaundecanol obtained in the above step 3, and then the solution was stirred overnight at 30° C. After concentrating the dichloromethane layer, the residue was purified with silica gel column chromatography to obtain 1.12 g of the objective compound.

Step 5. Synthesis of L-α-dioleoylphosphatidyl{11-N-(1-deoxylactito-1-yl)amino-3,6,9-trioxa}undecanol 600 mg of L-α-dioleoylphosphatidyl(11-amino-3,6,9-trioxa)undecanol obtained in the above step 4 and 247 mg of lactose monohydrate were dissolved in a mixture of 1 mL of water, 5 mL of methanol and 1 mL of dichloromethane. Subsequently, 0.6 mL of acetic acid and 86 mg of sodium cyanoborohydride were added, and then the solution was stirred overnight at 70° C. After concentrating the reaction solution, the objective compound was extracted by Bligh- Dyer method, and then 423 mg of the objective compound (the derivative of the present invention) was obtained by purifying with silica gel column chromatography.

ESI-Mass (m/z)=1200.9 ([M–H]$^-$)

Example 6

Synthesis of L-α-dioleoylphosphatidyl{29-N-(1-deoxylactito-1-yl)amino-3,6,9,12,15,18,21,24,27-nonaoxa}oxanonacosanol Step 1. Synthesis of 11-azide-1-{(methylsulfonyl)oxy}-3,6,9-trioxaundecane 13.5 g of 11-azide-3,6,9-trioxaundecanol obtained in the step 2 of Example 5 and 12.5 g of triethylamine were dissolved in 200 mL of dichloromethane, to which 9.2 g of methanesulfonyl chloride was added dropwise at 0° C., and then the solution was stirred at room temperature for 1 hour. Subsequently, the reaction solution was concentrated under reduced pressure. After adding ethyl acetate/hexane (1/1), insolubles were removed by filtration, and then the filtrate was concentrated under reduced pressure. The residue was purified with silica gel column chromatography to obtain 15.3 g of the objective compound.

Step 2. Synthesis of 19,19,19-triphenyl-3,6,9,12,15,18-hexaoxanonadecanol 25 g of hexaethyleneglycol was dissolved in a mixture of 100 mL of acetonitrile and 30 mL of pyridine, to which 12.5 g of trityl chloride was added at 0° C., and then the solution was stirred overnight at room temperature. The reaction solution was mixed with iced water and subjected to extraction with ethyl acetate, and then the organic layer washed with water and concentrated under reduced pressure after drying. The residue was purified with silica gel column chromatography to obtain 15.7 g of the objective compound.

Step 3. Synthesis of 1-azide-31,31,31-triphenyl-3,6,9,12,15,18,21,24,27,30-decaoxahentriacontanol 15 g of 19,19,19-triphenyl-3,6,9,12,15,18-hexaoxanonadecanol obtained in the above step 2 was dissolved in 100 mL of dimethylformamide. The solution was added dropwise to a suspension containing 1.3 g of sodium hydride in 50 mL of dimethylformamide at 0° C. After stirring at room temperature for 1 hour, the solution was again cooled at 0° C., and then a solution of 7 g of 11-azide-1-(methylsulfonyl)oxy-3,6,9-trioxaundecane obtained in the above step 1 in 50 mL of dimethylformamide was added dropwise. Subsequently, the solution was stirred at 110° C. for 2 hours. The reaction solution was mixed with iced water and subjected to extraction with ethyl acetate, and then the organic layer washed with water and concentrated under reduced pressure after drying. The residue was purified with silica gel column chromatography to obtain 10.5 g of the objective compound.

Step 4. Synthesis of 29-azide-3,6,9,12,15,18,21,24,27-nonaoxanonacosanol 10.3 g of 1-azide-31,31,31-triphenyl-3,6,9,12,15,18,21,24,27,30-decaoxahentriacontanol obtained in the above step 3 was dissolved in 41 mL of 0.38 M benzenesulfonic acid methanol solution, and then 50 mL of water was added after the solution was stirred at room temperature for 10 minutes. Then, the methanol layer was concentrated under reduced pressure. The residue washed with pentan, and then the aqueous layer was lyophilized. The residue was purified with silica gel column chromatography to obtain 6.7 g of the objective compound.

Step 5. Synthesis of 29-amino-3,6,9,12,15,18,21,24,27-nonaoxanonacosanol 6.5 g of 29-azide-3,6,9,12,15,18,21,24,27-nonaoxanonacosanol obtained in the above step 4 was dissolved in 60 mL of methanol, and then the solution was hydrogenated for 6 hours in the presence of 1 g of 10% palladium/carbon. The reaction solution was filtered, and then the filtrate was concentrated under reduced pressure. Then, the residue was purified with silica gel column chromatography to obtain 4.7 g of the objective compound.

Step 6. Synthesis of L-α-dioleoylphosphatidyl(29-amino-3,6,9,12,15,18,21,24,27-nonaoxa)nonacosanol 25 mL of dichloromethane, 3.5 mL of a buffer solution [sodium acetate (100 mM)—calcium chloride (50 mM) buffer solution (pH 6.5)] and 500 units of phospholipase D were added to 1 g of L-α-dioleoylphosphatidylcholine and 3.6 g of 29-amino-3,6,9,12,15,18,21,24,27-nonaoxanonacosanol obtained in the above step 5, and then the solution was stirred overnight at 30° C. After concentrating the dichloromethane layer, the residue was purified with silica gel column chromatography to obtain 660 mg of the objective compound.

Step 7. Synthesis of L-α-dioleoylphosphatidyl{29-N-(1-deoxylactito-1-yl)amino-3,6,9,12,15,18,21,24,27-nonaoxa}nonacosanol 500 mg of L-α-dioleoylphosphatidyl(29-amino-3,6,9,12,15,18,21,24,27-nonaoxa)nonacosanol obtained in the above step 6 and 158 mg of lactose monohydrate were dissolved in a mixture of 1 mL of water, 5 mL of methanol and 1 mL of dichloromethane. Subsequently, 0.6 mL of acetic acid and 55 mg of sodium cyanoborohydride were added, and then the solution was stirred overnight at 70° C. After concentrating the reaction solution, the objective compound was extracted by Bligh-Dyer method, and 320 mg of the objective compound (the derivative of the present invention) was obtained by purifying with silica gel column chromatography.

ESI-Mass (m/z)=1465.0 ([M–H]$^-$)

Example 7

Synthesis of 2-O-[2-{N-(1-deoxylactito-1-yl)-N-ethyl}aminoethyl]carbamoyl-1,3-O-dioleoylglycerol 300 mg of 2-O-2-N-(1-deoxylactito-1-yl)aminoethylcarbamoyl-1,3-O-dioleoylglycerol obtained in Example 1 and 39 mg of acetaldehyde were dissolved in a mixture of 14 mL of methanol and 7 mL of dichloromethane. Subsequently, 1 mL of acetic acid and 109 mg of sodium cyanoborohydride were added, and then the solution was stirred overnight at 50° C. After concentrating the reaction solution, the objective compound was extracted by Bligh-Dyer method, and 200 mg of the objective compound (the derivative of the present invention) was obtained by purifying with silica gel column chromatography.

ESI-Mass (m/z)=1062.0 ([M+H]$^+$)

Example 8

Synthesis of 2-O-{11-N-(1-deoxylactito-1-yl)amino-3,6,9-trioxaundecyl}carbamoyl-1,3-O-dioleoylglycerol

Step 1. Synthesis of 1,11-di{(methylsulfonyl)oxy}-3,6,9-trioxaundecane 15 g of tetraethyleneglycol and 23.4 g of triethylamine were dissolved in 200 mL of dichloromethane, to which 22.1 g of methanesulfonylchloride was added dropwise at 0° C., and then the solution was stirred for 1 hour. The reaction solution was filtrated to remove insolubles, and then the filtrate was concentrated under reduced pressure. The residue was separated with ethyl acetate-water, and the organic layer was concentrated under reduced pressure after washing with water. The residue was purified with silica gel column chromatography to obtain 27 g of the objective compound.

Step 2. Synthesis of 1,11-diazido-3,6,9-trioxaundecane

In 300 mL of dimethylformamide, 23 mL of 1,11-di(methylsulfonyl)oxy-3,6,9-trioxaundecane obtained in the above step 1 and 12.8 g of sodium azide were stirred at 110° C. for 2 hours, and then the solution was mixed with iced water. The solution was extracted with ethyl acetate, and the organic layer washed with water and concentrated under reduced pressure after drying. The residue was purified with silica gel column chromatography to obtain 13.8 g of the objective compound.

Step 3. Synthesis of 1,11-diamino-3,6,9-trioxaundecane 13.5 g of 1,11-diazido-3,6,9-trioxaundecane obtained in the above step 2 was dissolved in 350 mL of tetrahydrofuran, and 31.9 g of triphenylphosphine was added. After stirring at room temperature overnight, 50 mL of water was added, and then the solution was further stirred overnight. The reaction solution was separated with toluene and water, and then the aqueous layer was lyophilized to obtain 10.4 g of the objective compound.

Step 4. Synthesis of 11-t-butoxycarbonylamino-3,6,9-trioxaundecylamine 3 g of 1,11-diamino-3,6,9-trioxaundecane obtained in the above step 3 was dissolved in 5 mL of tetrahydrofuran, and then a solution of 1.14 of di-t-butyl dicarbonate in 5 mL of tetrahydrofuran was added dropwise under ice cooling. Then, the solution was stirred overnight at room temperature, and concentrated under reduced pressure. The residue was dissolved in ethyl acetate, and then the solution washed with saturated saline. The organic layer was dried, and then concentrated under reduced pressure. The residue was purified with silica gel column chromatography to obtain 1 g of the objective compound.

Step 5. Synthesis of 2-O-(11-amino-3,6,9-trioxaundecyl)carbamoyl-1,3-O-dioleoylglycerol According to the step 2 of Example 1, 800 mg of the objective compound was prepared by using 650 mg of 11-t-butoxycarbonylamino-3,6,9-trioxaundecylamine obtained in the above step 4 instead of N-(t-butoxycarbonyl)-1,2-ethylenediamine.

Step 6. Synthesis of 2-O-{11-N-(1-deoxylactito-1-yl)amino-3,6,9-trioxaundecyl}carbamoyl-1,3-O-dioleoylglycerol 700 mg of 2-O-(11-amino-3,6,9-trioxaundecyl)carbamoyl-1,3-O-dioleoylglycerol obtained in the above step 5 and 300 mg of lactose monohydrate were dissolved in a mixture of 1 mL of water, 5 mL of methanol and 1 mL of dichloromethane. Subsequently, 0.8 mL of acetic acid and 157 mg of sodium cyanoborohydride were added, and then the solution was stirred overnight at 70° C. After concentrating the reaction solution, the objective compound was extracted by Bligh-Dyer method, and 508 mg of the objective compound (the derivative of the present invention) was obtained by purifying with silica gel column chromatography.

ESI-Mass (m/z)=1165.9 ([M+H]$^+$)

Example 9

Preparation of the Dispersion Liquid of the Carrier of the Present Invention (1)

In a vial, 3.75 mg of 2-O-(2-diethylaminoethyl)carbamoyl-1,3-O-dioleoylglycerol, 1.25 mg of the derivative of the present invention according to Example 2 and 5 mg of egg yolk lecithin were dissolved in 0.5 mL of chloroform. Then, chloroform was removed under nitrogen gas atmosphere, leaving a thin film on the internal wall of the vial. The vial was then allowed to stand overnight under reduced pressure and, after addition of 1.995 mL of 10% maltose solution and 5 μL of 1 N HCl, was agitated with a vortex mixer to exfoliate the film. After leaving at 4° C. for 3 hours, the carrier of the present invention at 5 mg/mL was prepared by sonicating for one minute with a microprobe.

Example 10

Preparation of the Dispersion Liquid of the Carrier of the Present Invention (2)

Using 3.75 mg of 2-O-(2-diethylaminoethyl)carbamoyl-1,3-O-dioleoylglycerol, 2.5 mg of the derivative of the present invention according to Example 2 and 3.75 mg of egg yolk lecithin, the dispersion liquid of the carrier of the present invention was prepared in the same manner as in Example 9.

Example 11

Preparation of the Dispersion Liquid of the Carrier of the Present Invention (3)

Using 3.75 mg of 2-O-(2-diethylaminoethyl)carbamoyl-1,3-O-dioleoylglycerol, 3.75 mg of the derivative of the present invention according to Example 2 and 2.5 mg of egg yolk lecithin, the dispersion liquid of the carrier of the present invention was prepared in the same manner as in Example 9.

Example 12

Preparation of the Dispersion Liquid of the Carrier of the Present Invention (4)

Using 3.75 mg of 2-O-(2-diethylaminoethyl)carbamoyl-1,3-O-dioleoylglycerol, 5 mg of the derivative of the present invention according to Example 2 and 1.25 mg of egg yolk lecithin, the dispersion liquid of the carrier of the present invention was prepared in the same manner as in Example 9.

Example 13

Preparation of the Dispersion Liquid of the Carrier of the Present Invention (5)

Using 3.75 mg of 2-O-(2-diethylaminoethyl)carbamoyl-1,3-O-dioleoylglycerol and 6.25 mg of the derivative of the present invention according to Example 2, the dispersion liquid of the carrier of the present invention was prepared in the same manner as in Example 9.

Example 14

Preparation of the Dispersion Liquid of the Carrier of the Present Invention (6)

Using 3.75 mg of 2-O-(2-diethylaminoethyl)carbamoyl-1,3-O-dioleoylglycerol, 3.75 mg of the compound according to Reference Example 1 and 2.5 mg of egg yolk lecithin, the dispersion liquid of the carrier of the present invention was prepared in the same manner as in Example 9.

Example 15

Preparation of the Dispersion Liquid of the Carrier of the Present Invention (7)

Using 3.75 mg of 2-O-(2-diethylaminoethyl)carbamoyl-1,3-O-dioleoylglycerol, and 6.25 mg of the compound according to Reference Example 1, the dispersion liquid of the carrier of the present invention was prepared in the same manner as in Example 9.

Comparative Example 1

Preparation of the Dispersion Liquid of the Comparative Carrier

Using 3.75 mg of 2-O-(2-diethylaminoethyl)carbamoyl-1,3-O-dioleoylglycerol and 6.25 mg of egg yolk lecithin, the dispersion liquid of the comparative carrier was prepared in the same manner as in Example 9.

Test Example 1

(1) Preparation of the Compositions

By adding 50 µL of 10% maltose solution to 1 µg of the plasmid DNA encording luciferase gene, 50 µL of the plasmid solution containing the plasmid at 20 µg/mL was prepared. In addition, by adding 44 µL of 10% maltose solution to 6 µL of the dispersion liquid of the carrier according to Example 9 to 13 or Comparative Example 1, 50 µL of the diluted solution of the carrier at 600 µg/mL was prepared.

50 µL of the above nucleic acid solution was added to 50 µL of the above diluted solution of the carrier, and then mixed gently. Then, the sample was left at room temperature for 15 minutes to prepare 100 µL of the composition solution containing the above plasmid at 10 µg/mL.

(2) Method of Experiment

HuH-7 cells (human hepatoma cell line) were seeded on a 96-well plate at $1 \times 10^4$ cells/well, and were incubated for 18 hours at 37° C. under 5% $CO_2$. Then, 10 µL of the composition containing the carrier according to Example 9 to 13 or Comparative Example 1 prepared above (1) was added per well, and incubation was further continued. After 24 hours from addition of the composition, luciferase activity was measured. Luciferase activity was measured by detecting the bioluminescence with Top Count (manufactured by Packard), using Steady Glo Luciferase Assay System (manufactured by Promega). Meanwhile, a comparative control was a cell given the composition containing the carrier according to Comparative Example 1.

(3) Result

As shown in FIG. 1, when the composition of the present invention containing the derivative of the present invention according to Example 2 was used, expression efficiency of luciferase gene contained in the composition of the present invention was increased as compared with that in the comparative control as a function of concentration of the derivative of the present invention.

Test Example 2

(1) Preparation of the Compositions

By dissolving the control siRNA labeled with Alexa Fluor 488 (manufactured by Qiagen, Cat # 1,022, 563 and used hereinafter) in water for injection, the solution containing the siRNA at 20 µM (herein after referred to as "the nucleic acid stock solution") was prepared. By adding 45 µL of 10% maltose solution to 5 µL of the above nucleic acid stock solution, 50 µL of the solution containing the above siRNA at 2 µM (herein after referred to as "the nucleic acid diluted solution") was prepared. In addition, by adding 45.5 µL of 10% maltose solution to 4.5 µL of the dispersion liquid of the carrier according to Example 13, 14 or Comparative Example 1, 50 µL of the diluted solution of the carrier at 450 µg/mL was prepared. 50 µL of the above diluted solution of the nucleic acid was added to 50 µL of the above diluted solution of the carrier, and then mixed gently. Then, the sample was left at room temperature for 15 minutes to prepare 100 µL of the composition solution containing the above siRNA at 1 µM.

(2) Method of Experiment

HuH-7 cells were seeded on a 6-well plate at $4 \times 10^5$ cells/well, and were incubated for 18 hours at 37° C. under 5% $CO_2$. Then, the composition containing the carrier according to Example 13, 14 or Comparative Example 1 prepared above (1) was added per well so that the final concentration of siRNA was 100 nM, and incubation was further continued. After 24 hours from addition of the composition, the cells were washed 2 times with phosphate buffered saline (pH 7.4) (herein after referred to as "PBS"), and were taken off from the plate with 500 µL of a trypsin/EDTA (manufactured by Sigma) and collected in Eppendorf Tube. After centrifuging at 3000 rpm for 3 minutes, the supernatant was removed, and the cells were resuspended with 1 mL of PBS. Further, after centrifuging at 3000 rpm for 3 minutes, the supernatant was removed, and the cells were resuspended with 0.5 mL of PBS. The fluorescence intensity of a single cell was measured by using FACS Calibar (registeredmark) (manufactured by Beckton Dickinson). Meanwhile, a comparative control was a cell given the composition containing the carrier according to Comparative Example 1, and a negative control was a non-treated cell.

(3) Result

FIG. 2 shows the result with the composition of the present invention containing the carrier of the present invention according to Example 13, and FIG. 3 shows the result with the composition of the present invention containing the carrier of the present invention according to Example 14. From these results, both compositions including the carrier of the present invention according to Example 13 and 14 have a targeting property to hepatocytes.

Test Example 3

(1) Preparation of an Oligo Double-Stranded RNA Solution

The oligo RNA having a sequence of sequence No. 1 and the oligo RNA having a sequence of sequence No. 2 were each dissolved in water for injection so that the concentration of each solution was 100 μM, and 20 μL of each solution was mixed. By adding 60 μL of water for injection to this mixture, the solution containing each oligo RNA at 20 μM (herein after referred to as "the nucleic acid solution") was prepared. Meanwhile, the synthesis of the above two oligo RNAs was requested of Japan Bio Services Co., LTD.

(2) Preparation of Compositions

100 μL of the composition containing an oligo RNA at 1 μM was prepared in the same manner as in Test Example 2•(1) by using the dispersion liquid according to Example 15 or Comparative Example 1 and the nucleic acid solution prepared in the above process (1) as the nucleic acid stock solution.

(3) The Cell Line Used

In the following (4), the HuH-7 cell caffying the replicon of HCV was used. The cell was transfected with the replicon RNA of HCV which encodes a neomycin resistance gene in a region cording a genomic structural protein of HCV. In the cell, NPTII which is a product of the neomycin resistance gene was expressed through autonomous replication of the replicon. The details of the cell have been reviewed in the reference (Biochemical and Biophysical Research Communications, 2002, vol. 293, p. 993-999). Meanwhile, as a culture medium at the time of evaluation, DMEM medium containing 10% FBS was used. Except for the time of evaluation, a culture medium which further comprised G418 (manufactured by Invitrogen) at 400 μg/ml in the above culture medium was used.

(4) Method of Experiment

The cells were seeded on a 12-well plate at $5\times10^4$ cells/well, and incubated overnight at 37° C. under 5% $CO_2$. The next day, the culture medium was removed from the plate under suction, and 0.9 mL of the culture medium was added. Then, 0.1 mL of the composition containing the carrier according to Example 15 or Comparative Example 1 prepared in the above (2) was added per well to give an arbitrary final concentration. After culturing the cell in a $CO_2$ incubator for 24 hours from the addition of the composition, the cells were washed 2 times with PBS. Then, the cells were taken off from the plate, and protein was extracted.

The concentration of NPTII in the extracted protein was measured by Patho Screen Kit for NPTII (manufactured by Agdia). Meanwhile, the extraction of protein was performed by using an extraction buffer attached to the kit. In addition, the total protein concentration of the extracted protein was measured by BCA Protein Assay (manufactured by Pierce). Meanwhile, a comparative control was a cell given the composition containing the carrier according to Comparative Example 1, and a negative control was a cell given 10% maltose solution instead of the composition prepared in the above (2).

(5) Method of Evaluation

The evaluation was performed by comparing expression rate of NPTII regarding the amount of NPTII per unit of protein obtained by the addition of the negative control as 100%. The lower expression rate of NPTII means the stronger inhibition of the replicon replication.

(6) Result

As shown in FIG. 4, when the composition of the present invention containing the carrier of the present invention according to Example 15 was used, the replication of replicon was inhibited more strongly than the comparative control.

All publications, patents, articles, and other references cited and/or discussed in this specification are incorporated herein by reference in their entirety and to the same extent as if each reference was individually incorporated by reference.

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial sequence
<220> FEATURE:
<223> OTHER INFORMATION: synthesized DNA/RNA; a strand, wherein 2
      nucleotides of 3'-terminus are constructed with DNA, and the rest
      are RNA.

<400> SEQUENCE: 1
guaguguugg gucgcgaaat t                                           21

<210> SEQ ID NO 2
<211> LENGTH: 21
<212> TYPE: DNA
<213> ORGANISM: Artificial sequence
<220> FEATURE:
<223> OTHER INFORMATION: synthesized DNA/RNA; a strand, wherein 2
      nucleotides of 3'-terminus are constructed with DNA, and the rest
      are RNA.

<400> SEQUENCE: 2
uuucgcgacc caacacuact t                                           21
```

The invention claimed is:

1. A galactose derivative represented general formula (I),

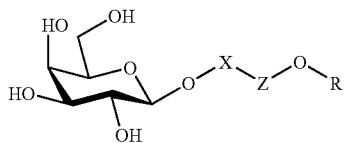
(I)

wherein, X represents the following formula (II) or (III); Z represents the following formula (IV) or (V); R represents the following formula (VI) or (VII);

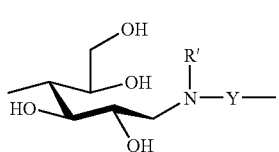
(II)

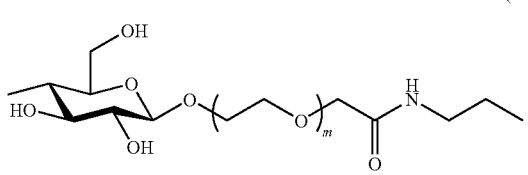
(III)

(IV)

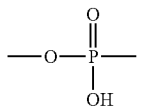
(V)

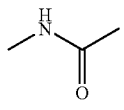
(VI)

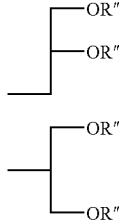
(VII)

Y represents the following formula (VIII) or (IX); R' represents hydrogen or an alkyl having 1 to 10 optionally substituted carbon atoms; R" represents a saturated or unsaturated aliphatic hydrocarbon group having 10 to 30 carbon atoms, or a saturated or unsaturated fatty acid residue having 10 to 30 carbon atoms;

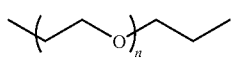
(VIII)

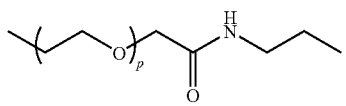
(IX)

each of m and p independently represents an integer from 0 to 50, and n represents an integers from 1 to 50, excluding the following galactose derivatives:

(1) 1,2-dioleoyl-sn-glycero-3-phosphatidyl-N-(1-deoxy-lactito-1-yl)ethanolamine, (2) galactose derivatives in which X is formula (II), Y is formula (VIII), Z is formula (IV), and R is formula (VII) in the general formula (I), (3) galactose derivatives in which X is formula (II), Y is formula (IX), Z is formula (IV), and R is formula (VII) in the general formula (I), and (4) galactose derivatives in which X is formula (III), Z is formula (IV), and R is formula (VII) in the general formula (I).

2. A galactose derivative selected from:

(1) 2-O-{2-N-(1-deoxylactito-1-yl)aminoethyl} carbamoyl-1,3-O-dioleoyl glycerol, (2) L-α-dioleoyl phosphatidyl{14-N-(1-deoxylactito-1-yl)amino-3,6,9,12-tetraoxa}tetra decanol, (3) L-α-dioleoyl phosphatidyl-N-{14-(β-1-lactosyloxy)-3,6,9,12-tetraoxa tetradecoxy acetyl}ethanolamine, (4) 2-O-[2-N-{14-(β-1-lactosyloxy)-3,6,9,12-tetraoxa tetradecoxy acetyl}aminoethyl]carbamoyl-1,3-dioleoyl glycerol, (5) L-α-dioleoyl phosphatidyl{11-N-(1-deoxylactito-1-yl)amino-3,6,9-trioxa}undecanol, (6) L-α-dioleoyl phosphatidyl{29-N-(1-deoxylactito-1-yl)amino-3,6,9,12,15,18,21,24,27-nonaoxa}nonacosanol, (7) 2-O-[2-{N-(1-deoxylactito-1-yl)-N-ethyl}aminoethyl] carbamoyl-1,3-O-dioleoyl glycerol, and (8) 2-O-{11-N-(1-deoxylactito-1-yl)amino-3,6,9-trioxa undecyl}carbamoyl-1,3-O-dioleoyl glycerol.

3. A drug carrier, comprising a galactose derivative represented by general formula (I) and a cationic lipid,

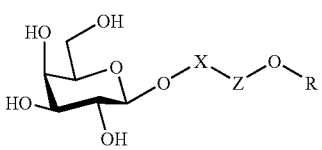
(I)

wherein, X represents the following formula (II) or (III); Z represents the following formula (IV) or (V); R represents the following formula (VI) or (VII);

(II)

(III)

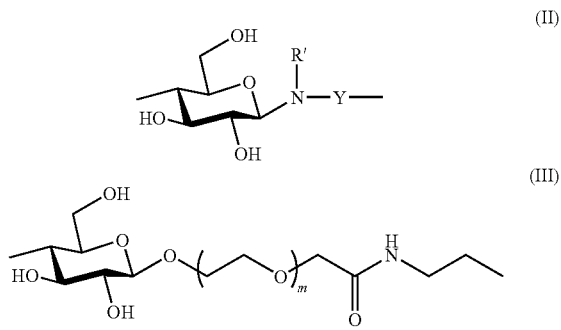

-continued

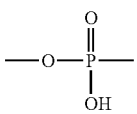 (IV)

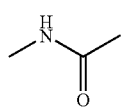 (V)

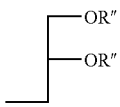 (VI)

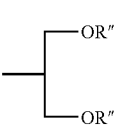 (VII)

Y represents the following formula (VIII) or (IX); R' represents hydrogen or an alkyl having 1 to 10 optionally substituted carbon atoms; R" represents a saturated or unsaturated aliphatic hydrocarbon group having 10 to 30 carbon atoms, or a saturated or unsaturated fatty acid residue having 10 to 30 carbon atoms;

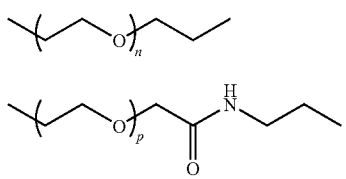 (VIII)

(IX)

and each of m and p independently represents an integer from 0 to 50 and n represents an integer from 1 to 50, excluding the following galactose derivatives:

(1) galactose derivatives in which X is formula (II), Y is formula (VIII), Z is formula (IV), and R is formula (VII) in the general formula (I), (2) galactose derivatives in which X is formula (II), Y is formula (IX), Z is formula (IV), and R is formula (VII) in the general formula (I), (3) galactose derivatives in which X is formula (III), Z is formula (IV), and R is formula (VII) in the general formula (I), and (4) 1,2-dioleoyl-sn-glycero-3-phosphatidyl-N-(1-deoxy-lactito-1-yl)ethanolamine.

4. The drug carrier according to claim 3, wherein the cationic lipid is 2-O-(2-diethylaminoethyl)carbamoyl-1,3-O-dioleoylglycerol.

5. The drug carrier according to claim 3, further comprising a phospholipid.

6. A pharmaceutical composition comprising a medicine and the drug carrier according to claim 3.

7. The pharmaceutical composition according to claim 6, wherein the medicine is a double-stranded RNA, a double-stranded DNA, an oligo nucleic acid or a water-soluble anion compound.

8. The pharmaceutical composition according to claim 7, wherein the oligo nucleic acid is an siRNA, an miRNA, an shRNA, an antisense DNA, an antisense RNA, a DNA enzyme, a ribozyme or an aptamer.

* * * * *